US009567375B2

(12) United States Patent
Luo et al.

(10) Patent No.: US 9,567,375 B2
(45) Date of Patent: Feb. 14, 2017

(54) CHIMERIC PESTIVIRUSES

(75) Inventors: Yugang Luo, Kalamazoo, MI (US); Siao-Kun Wan Welch, Kalamazoo, MI (US); Ying Yuan, Kalamazoo, MI (US); Robert Gerard Ankenbauer, Portage, MI (US)

(73) Assignee: Zoetis Services LLC, Parsippany, NJ (US)

( * ) Notice: Subject to any disclaimer, the term of this patent is extended or adjusted under 35 U.S.C. 154(b) by 695 days.

(21) Appl. No.: 12/624,473

(22) Filed: Nov. 24, 2009

(65) Prior Publication Data

US 2010/0136055 A1 Jun. 3, 2010

Related U.S. Application Data

(60) Provisional application No. 61/119,594, filed on Dec. 3, 2008, provisional application No. 61/173,363, filed on Apr. 28, 2009.

(51) Int. Cl.

*A61K 39/12* (2006.01)
*A61K 39/00* (2006.01)
*C12N 7/00* (2006.01)
*C07K 14/005* (2006.01)

(52) U.S. Cl.

CPC ............... *C07K 14/005* (2013.01); *C12N 7/00* (2013.01); *A61K 2039/525* (2013.01); *A61K 2039/5256* (2013.01); *C12N 2770/24322* (2013.01); *C12N 2770/24361* (2013.01)

(58) Field of Classification Search

None
See application file for complete search history.

(56) References Cited

U.S. PATENT DOCUMENTS

| | | | |
|---|---|---|---|
| 5,580,859 | A | 12/1996 | Felgner et al. |
| 5,589,466 | A | 12/1996 | Felgner et al. |
| 5,593,873 | A | 1/1997 | Cochran et al. |
| 5,703,055 | A | 12/1997 | Felgner et al. |
| 6,001,613 | A | 12/1999 | Donis et al. |
| 6,015,795 | A | 1/2000 | van den Hurk et al. |
| 6,060,457 | A | 5/2000 | Elazhary et al. |

FOREIGN PATENT DOCUMENTS

| | | |
|---|---|---|
| WO | 00/09701 | 2/2000 |

OTHER PUBLICATIONS

Avalos-Ramirez "Evidence for the Presence of Two Novel *Pestivirus* Species" Virology 286:456-465; 2001.*
Chen et al, "Adjuvant Enhancement of Humoral Immune Response to Chemically Inactivated Bovine Viral Diarrhea Virus," Can J Comp Med 49: pp. 91-94 (1985).*
Vilcek et al., "Characterization of a novel pestivirus originating from a pronghorn antelope," Virus Research 108, pp. 187-193 (2005).*
Peters et al., "Duration of immunity of a quadrivalent vaccine against respiratory diseases caused by BHV-1, PI3V, BVDV, and BRSV in experimentally infected calves," Preventative Veterinary Medicine 66 (pp. 63-77) (2004).*
Tautz et al., "Serine Protease of Pestiviruses: Determination of Cleavage Sites", J. Virol., 71(7):5415-5422 (1997).
Xu et al., "Bovine Viral Diarrhea Virus NS3 Serine Proteinase: Polyprotein Cleavage Sites, Cofactor Requirements, and Molecular Model of an Enzyme Essential for Pestivirus Replication", J. Virol., 71(7):5312-5322 (1997).
Elbers et al., "Processing in the Pestivirus E2-NS2 Region: Identification of Proteins p7 and E2p7", J. Virol., 70(6): 4131-4135 (1996).
Wiskerchen and Collett, "Pestivirus gene expression: protein p80 of bovine viral diarrhea virus is a proteinase involved in polyprotein processing", Virology, 184(1):341-350 (1991).
Martin et al., "Evaluation of Various BVDV Isolates to Induce Protection Against Challenge with Virulent BVDV ncp890", Proceedings of the Conference of Research Workers in Animal Diseases, 75:183 (1994).
Vassilev et al., "Authentic and Chimeric Full-Length Genomic cDNA Clones of Bovine Viral Diarrhea Virus That Yield Infectious Transcripts", J. Virol., 71(1):471-478 (1997).
Rasmussen et al., "Virulence, immunogenicity and vaccine properties of a novel chimeric pestivirus", J. Gen. Virol., 88(Pt 2):481-486 (2007).
Koenig et al., "CP7_E2alf: A safe and efficient marker vaccine strain for oral immunisation of wild boar against Classical swine fever virus (CSFV)", Vaccine, 25(17):3391-3399 (2007).
Reimann et al., "An avirulent chimeric Pestivirus with altered cell tropism protects pigs against lethal infection with classical swine fever virus", Virology, 322:143-157 (2004).
Ronecker et al., "Formation of Bovine Viral Diarrhea Virus E1-E2 Heterodimers is Essential for Virus Entry and Depends on Charged Residues in the Transmembrane Domains", J. Gen Virol., 89(9):2114-2121 (2008).
Van Gennip et al., "Chimeric Classical Swine Fever Viruses Containing Envelope Protein E<RNS> or E2 of Bovine Viral Diarrhoea Virus Protect Pigs Against Challenge with CSFV and Induce a Distinguishable Antibody Response", Vaccine, 19(4-5):447-459 (2000).
Dong et al., "Marker Vaccine Strategies and Candidate CSFV Marker Vaccines", Vaccine, 25(2):205-230 (2006).
Beer et al., "Novel Marker Vaccines Against Classical Swine Fever", Vaccine, 25(30):5665-5670 (2006).
De Smit et al., "Chimeric (Marker) C-strain Viruses Induce Clinical Protection Against Virulent Classical Swine Fever Virus (CSFV) and Reduce Transmission of CSFV Between Vaccinated Pigs", Vaccine, 19(11-12):1467-1476 (2001).
Gripshover et al., "Variation in Erns Viral Glycoprotein Associated with Failure of Immunohistochemistry and Commercial Antigen Capture ELISA to Detect a Field Strain of Bovine Viral Diarrhea Virus", Veterinary Microbiology, 125:11-21 (2007).

(Continued)

*Primary Examiner* — Janet L Andres
*Assistant Examiner* — M. Franco Salvoza
(74) *Attorney, Agent, or Firm* — E. Victor Donahue

(57) ABSTRACT

The present invention relates to chimeric pestiviruses having utility as immunogenic compositions and vaccines. Also described herein are methods and kits for treating or preventing the spread of bovine viral diarrhea virus infection, as well as methods and kits for differentiating between vaccinated and wild-type infected animals.

24 Claims, No Drawings

(56) References Cited

OTHER PUBLICATIONS

Grego et al., "Development and Application of an Enzyme-linked Immunosorbent Assay for Detection of Bovine Viral Diarrhea Antibody Based on Erns Glycoprotein Expressed in a Baculovirus System", J. Vet. Diagn. Invest., 19(1):21-27 (2007).

Vilcek et al., "Pestiviruses in Wild Animals", Veterinary Microbiology, 116(1-3):1-12 (2006).

Wehrle et al., "Chimeric Pestiviruses: Candidates for Live-attenuated Classical Swine Fever Marker Vaccines", J. Gen. Virol., 88(8):2247-2258 (2007).

PCT International Search Report, PCT/IB2009/055291, Mar. 17, 2010.

* cited by examiner

SEQUENCE LISTING

```
<160> NUMBER OF SEQ ID NOS: 32

<210> SEQ ID NO 1
<211> LENGTH: 43
<212> TYPE: DNA
<213> ORGANISM: Artificial Sequence
<220> FEATURE:
<223> OTHER INFORMATION: T7 + NADL
<220> FEATURE:
<221> NAME/KEY: misc_feature
<223> OTHER INFORMATION: Oligo B-5

<400> SEQUENCE: 1
```

-continued gtgttaatac gactcactat agtatacgag aattagaaaa ggc 43

<210> SEQ ID NO 2
<211> LENGTH: 21
<212> TYPE: DNA
<213> ORGANISM: Pestivirus
<220> FEATURE:
<221> NAME/KEY: misc_feature
<223> OTHER INFORMATION: NADL
<220> FEATURE:
<221> NAME/KEY: gene
<222> LOCATION: (1)..(21)
<223> OTHER INFORMATION: Oligo 84

<400> SEQUENCE: 2
gggggctgtt agaggtcttc c 21

<210> SEQ ID NO 3
<211> LENGTH: 47
<212> TYPE: DNA
<213> ORGANISM: Artificial Sequence
<220> FEATURE:
<223> OTHER INFORMATION: G-Erns+NADL
<220> FEATURE:
<221> NAME/KEY: misc_feature
<223> OTHER INFORMATION: Oligo 127

<400> SEQUENCE: 3
aattccactg ggtgatgttc tctcccattg taacttgaaa caaaact 47

<210> SEQ ID NO 4
<211> LENGTH: 20
<212> TYPE: DNA
<213> ORGANISM: Pestivirus
<220> FEATURE:
<221> NAME/KEY: misc_feature
<223> OTHER INFORMATION: G-Erns
<220> FEATURE:
<221> NAME/KEY: gene
<222> LOCATION: (1)..(20)
<223> OTHER INFORMATION: Oligo 128

<400> SEQUENCE: 4
gagaacatca cccagtggaa 20

<210> SEQ ID NO 5
<211> LENGTH: 21
<212> TYPE: DNA
<213> ORGANISM: Pestivirus
<220> FEATURE:
<221> NAME/KEY: misc_feature
<223> OTHER INFORMATION: G-Erns
<220> FEATURE:
<221> NAME/KEY: gene
<222> LOCATION: (1)..(21)
<223> OTHER INFORMATION: Oligo 129

<400> SEQUENCE: 5
tgcgtgggct ccaaaccatg t 21

<210> SEQ ID NO 6
<211> LENGTH: 44
<212> TYPE: DNA
<213> ORGANISM: Artificial Sequence
<220> FEATURE:
<223> OTHER INFORMATION: G-Erns+NADL
<220> FEATURE:
<221> NAME/KEY: misc_feature
<223> OTHER INFORMATION: Oligo 130

<400> SEQUENCE: 6
aacatggttt ggagcccacg cagcttcccc ttactgtgat gtcg 44

<210> SEQ ID NO 7
<211> LENGTH: 47
<212> TYPE: DNA
<213> ORGANISM: Artificial Sequence
<220> FEATURE:
<223> OTHER INFORMATION: R-Erns+NADL
<220> FEATURE:
<221> NAME/KEY: misc_feature
<223> OTHER INFORMATION: Oligo 131

<400> SEQUENCE: 7
ggttccactg tgttatattc tctcccattg taacttgaaa caaaact 47

<210> SEQ ID NO 8
<211> LENGTH: 22
<212> TYPE: DNA
<213> ORGANISM: Pestivirus
<220> FEATURE:
<221> NAME/KEY: misc_feature
<223> OTHER INFORMATION: R-Erns
<220> FEATURE:
<221> NAME/KEY: gene
<222> LOCATION: (1)..(22)
<223> OTHER INFORMATION: Oligo 132

<400> SEQUENCE: 8
gagaatataa cacagtggaa cc 22

<210> SEQ ID NO 9
<211> LENGTH: 22
<212> TYPE: DNA
<213> ORGANISM: Pestivirus
<220> FEATURE:
<221> NAME/KEY: misc_feature
<223> OTHER INFORMATION: R-Erns
<220> FEATURE:
<221> NAME/KEY: gene
<222> LOCATION: (1)..(22)
<223> OTHER INFORMATION: Oligo 133

<400> SEQUENCE: 9
tgcattagct ccgaaccacg tt 22

<210> SEQ ID NO 10
<211> LENGTH: 44
<212> TYPE: DNA
<213> ORGANISM: Artificial Sequence
<220> FEATURE:
<223> OTHER INFORMATION: R-Erns+NADL
<220> FEATURE:
<221> NAME/KEY: misc_feature
<223> OTHER INFORMATION: Oligo 134

<400> SEQUENCE: 10
aacgtggttc ggagctaatg cagcttcccc ttactgtgat gtcg 44

<210> SEQ ID NO 11
<211> LENGTH: 42
<212> TYPE: DNA
<213> ORGANISM: Artificial Sequence
<220> FEATURE:
<223> OTHER INFORMATION: P-Erns+NADL
<220> FEATURE:
<221> NAME/KEY: misc_feature
<223> OTHER INFORMATION: Oligo 135

<400> SEQUENCE: 11
ggttccactg agttatattc actcccattg taacttgaaa ca 42

<210> SEQ ID NO 12
<211> LENGTH: 22
<212> TYPE: DNA
<213> ORGANISM: Pestivirus
<220> FEATURE:
<221> NAME/KEY: misc_feature
<223> OTHER INFORMATION: P-Erns
<220> FEATURE:
<221> NAME/KEY: gene
<222> LOCATION: (1)..(22)
<223> OTHER INFORMATION: Oligo 136

<400> SEQUENCE: 12
gtgaatataa ctcagtggaa cc 22

<210> SEQ ID NO 13
<211> LENGTH: 21
<212> TYPE: DNA
<213> ORGANISM: Pestivirus
<220> FEATURE:
<221> NAME/KEY: misc_feature
<223> OTHER INFORMATION: P-Erns
<220> FEATURE:
<221> NAME/KEY: gene
<222> LOCATION: (1)..(21)
<223> OTHER INFORMATION: Oligo 137

<400> SEQUENCE: 13
tgcctgtgcc ccaaaccatg t 21

<210> SEQ ID NO 14
<211> LENGTH: 44
<212> TYPE: DNA
<213> ORGANISM: Artificial Sequence
<220> FEATURE:
<223> OTHER INFORMATION: P-Erns+NADL
<220> FEATURE:
<221> NAME/KEY: misc_feature
<223> OTHER INFORMATION: Oligo 138

<400> SEQUENCE: 14
aacatggttt ggggcacagg cagcttcccc ttactgtgat gtcg 44

<210> SEQ ID NO 15
<211> LENGTH: 23
<212> TYPE: DNA
<213> ORGANISM: Pestivirus
<220> FEATURE:
<221> NAME/KEY: misc_feature
<223> OTHER INFORMATION: NADL
<220> FEATURE:
<221> NAME/KEY: gene
<222> LOCATION: (1)..(23)
<223> OTHER INFORMATION: Oligo 175

<400> SEQUENCE: 15
gttatcaata gtagccacag aat 23

<210> SEQ ID NO 16
<211> LENGTH: 22
<212> TYPE: DNA
<213> ORGANISM: Pestivirus
<220> FEATURE:
<221> NAME/KEY: misc_feature
<223> OTHER INFORMATION: NADL
<220> FEATURE:

-continued

<221> NAME/KEY: gene
<222> LOCATION: (1)..(22)
<223> OTHER INFORMATION: Oligo 177

<400> SEQUENCE: 16
tccaccctca atcgacgcta aa 22

<210> SEQ ID NO 17
<211> LENGTH: 22
<212> TYPE: DNA
<213> ORGANISM: Pestivirus
<220> FEATURE:
<221> NAME/KEY: misc_feature
<223> OTHER INFORMATION: CM5960
<220> FEATURE:
<221> NAME/KEY: gene
<222> LOCATION: (1)..(22)
<223> OTHER INFORMATION: Oligo 237

<400> SEQUENCE: 17
ccctgaggcc ttctgttctg at 22

<210> SEQ ID NO 18
<211> LENGTH: 23
<212> TYPE: DNA
<213> ORGANISM: Pestivirus
<220> FEATURE:
<221> NAME/KEY: misc_feature
<223> OTHER INFORMATION: CM5960
<220> FEATURE:
<221> NAME/KEY: gene
<222> LOCATION: (1)..(23)
<223> OTHER INFORMATION: Oligo P7

<400> SEQUENCE: 18
cacttgtcgg aggtactact act 23

<210> SEQ ID NO 19
<211> LENGTH: 24
<212> TYPE: DNA
<213> ORGANISM: Pestivirus
<220> FEATURE:
<221> NAME/KEY: misc_feature
<223> OTHER INFORMATION: CM5960
<220> FEATURE:
<221> NAME/KEY: gene
<222> LOCATION: (1)..(24)
<223> OTHER INFORMATION: Oligo P8

<400> SEQUENCE: 19
cttgtctatc ttatctctta ttgc 24

<210> SEQ ID NO 20
<211> LENGTH: 22
<212> TYPE: DNA
<213> ORGANISM: Pestivirus
<220> FEATURE:
<221> NAME/KEY: misc_feature
<223> OTHER INFORMATION: CM5960
<220> FEATURE:
<221> NAME/KEY: gene
<222> LOCATION: (1)..(22)
<223> OTHER INFORMATION: Oligo P3

<400> SEQUENCE: 20
actatctgaa cagttggaca gg 22

<210> SEQ ID NO 21
<211> LENGTH: 41

<212> TYPE: DNA
<213> ORGANISM: Artificial Sequence
<220> FEATURE:
<223> OTHER INFORMATION: T7+CM53637
<220> FEATURE:
<221> NAME/KEY: misc_feature
<223> OTHER INFORMATION: Oligo 296-1

<400> SEQUENCE: 21
gtgttaatac gactcactat agtatacgag attagctaaa g 41

<210> SEQ ID NO 22
<211> LENGTH: 48
<212> TYPE: DNA
<213> ORGANISM: Artificial Sequence
<220> FEATURE:
<223> OTHER INFORMATION: P-Erns+CM53637
<220> FEATURE:
<221> NAME/KEY: misc_feature
<223> OTHER INFORMATION: Oligo 297

<400> SEQUENCE: 22
ccaggttcca ctgagttata ttcactcctg ttaccagctg aagcagaa 48

<210> SEQ ID NO 23
<211> LENGTH: 43
<212> TYPE: DNA
<213> ORGANISM: Artificial Sequence
<220> FEATURE:
<223> OTHER INFORMATION: P-Erns+CM53637
<220> FEATURE:
<221> NAME/KEY: misc_feature
<223> OTHER INFORMATION: Oligo 298

<400> SEQUENCE: 23
aacatggttt ggggcacagg cagcaagtcc atactgtaaa gtg 43

<210> SEQ ID NO 24
<211> LENGTH: 27
<212> TYPE: DNA
<213> ORGANISM: Pestivirus
<220> FEATURE:
<221> NAME/KEY: misc_feature
<223> OTHER INFORMATION: CM53637
<220> FEATURE:
<221> NAME/KEY: gene
<222> LOCATION: (1)..(27)
<223> OTHER INFORMATION: Oligo 299

<400> SEQUENCE: 24
ttaatgccct ccctgtctct accacct 27

<210> SEQ ID NO 25
<211> LENGTH: 25
<212> TYPE: DNA
<213> ORGANISM: Pestivirus
<220> FEATURE:
<221> NAME/KEY: misc_feature
<223> OTHER INFORMATION: CM53637
<220> FEATURE:
<221> NAME/KEY: gene
<222> LOCATION: (1)..(25)
<223> OTHER INFORMATION: Oligo 300

<400> SEQUENCE: 25
aggatgagga tctagcagtg gatct 25

<210> SEQ ID NO 26
<211> LENGTH: 24

<212> TYPE: DNA
<213> ORGANISM: Pestivirus
<220> FEATURE:
<221> NAME/KEY: misc_feature
<223> OTHER INFORMATION: CM53637
<220> FEATURE:
<221> NAME/KEY: gene
<222> LOCATION: (1)..(24)
<223> OTHER INFORMATION: Oligo 303

<400> SEQUENCE: 26
ccatagccat ctgctcagac agta 24

<210> SEQ ID NO 27
<211> LENGTH: 26
<212> TYPE: DNA
<213> ORGANISM: Pestivirus
<220> FEATURE:
<221> NAME/KEY: misc_feature
<223> OTHER INFORMATION: CM53637
<220> FEATURE:
<221> NAME/KEY: gene
<222> LOCATION: (1)..(26)
<223> OTHER INFORMATION: Oligo 92-1

<400> SEQUENCE: 27
ggggctgtca gaggcatcct ctagtc 26

<210> SEQ ID NO 28
<211> LENGTH: 24
<212> TYPE: DNA
<213> ORGANISM: Pestivirus
<220> FEATURE:
<221> NAME/KEY: misc_feature
<223> OTHER INFORMATION: CM53637
<220> FEATURE:
<221> NAME/KEY: gene
<222> LOCATION: (1)..(24)
<223> OTHER INFORMATION: Oligo 321

<400> SEQUENCE: 28
agccactaca cctgtcacga gaag 24

<210> SEQ ID NO 29
<211> LENGTH: 27
<212> TYPE: DNA
<213> ORGANISM: Artificial Sequence
<220> FEATURE:
<223> OTHER INFORMATION: NADL
<220> FEATURE:
<221> NAME/KEY: misc_feature
<223> OTHER INFORMATION: Oligo 250

<400> SEQUENCE: 29
caccatgaaa atagtgccca aagaatc 27

<210> SEQ ID NO 30
<211> LENGTH: 25
<212> TYPE: DNA
<213> ORGANISM: Artificial Sequence
<220> FEATURE:
<223> OTHER INFORMATION: NADL
<220> FEATURE:
<221> NAME/KEY: misc_feature
<223> OTHER INFORMATION: Oligo 252

<400> SEQUENCE: 30
ttaagcgtat gctccaaacc acgtc 25

<210> SEQ ID NO 31
<211> LENGTH: 12307
<212> TYPE: DNA
<213> ORGANISM: Artificial Sequence
<220> FEATURE:
<223> OTHER INFORMATION: Erns chimeric virus
<220> FEATURE:
<221> NAME/KEY: misc_feature
<223> OTHER INFORMATION: BVDV Type 1

<400> SEQUENCE: 31

```
gtatacgaga attagaaaag gctctcgtat acgtattggg caattaaaat aataattagg     60
cctagggaac aaaagtcccc ctcagcgaag gccgaaaaga ggctagccat gcccttagta    120
ggactagcat aaagaggggg gtagcagcag tggtgagttc gttggatggc ttaagccctg    180
agtacagggt agtcgtcagt ggttcgacgc cttggaataa aggtctcgag atgccacgtg    240
gacgagggca tgcccaaagc acatcttaac ctgagcgggg gtcgcccagg taaaagcagt    300
tctaaccgac tgttacgaat acagcctgat agggtgctgc agaggccttc tgttctgcta    360
ctaaaaatct ctgctgtaca tggcacatgg agttgatcac aaatgaactt ttatacaaaa    420
cttacaaaca aaaacccgtc agggtggaag aacctgttta tgatcaggca ggtgatccct    480
tatttggtga aaggggagca gtccaccctc aatcgacgtt aaagctccca cacaagagag    540
gggaatgcga tgtacccatc aacttggcat ctttaccaaa aaggggtgac tgcaggtcgg    600
gtaatagcag aggacctgtg agcgggatct acttgaagcc agggccacta ttttaccagg    660
actataaggg tcccgtctat cacagggccc cgctggagct ctttgaagag ggaaccatgt    720
gtgaaacgac taaacggata gggagagtaa ctggaagtga cggaaagttg taccacattt    780
atgtgtgtat agatggatgt ataataataa aaagtgccac aagaagtcac caaagggtgc    840
ttaggtgggt ccataatagg cttaactgcc ctctatgggt cacaagttgc tcagacacga    900
aagaagaggg agcaacaaaa aagaaaacac agaaacccga cagactagag aaggggaaga    960
tgaaaatagt gcccagagaa tccgaaaaag acagcaaaac taaacctccg gatgctacaa   1020
tagtggtaga tggagttaaa taccaggtga agaagaaggg aaaaatcaag agtaagaaca   1080
ctcaggacgg cttgtaccat aacaaaaaca aaccgccgga atcacgtaag aaactggaaa   1140
aagcattgct ggcatgggca ataataacta tagttttgtt tcaagttaca atgggagtga   1200
atataactca gtggaacctg gctgacgaag gcaccgaagg cgtacatagg gtcatgtttg   1260
agagagggat aaatagaagt ttacatggca tatggcccca acagatatgc cacggaatcc   1320
caagctacaa ccccaccaac agagagctct cgatgattgt cggaatggtt gatgcaagca   1380
ttagaacaaa ttatacctgc tgtaatctac agagacacga atggaacaaa catggctggt   1440
gcaattggta caacatcata ccatggatta aggtgatgaa ctacagccag aggaacctca   1500
ctgaaggcac atatggcaaa gagtgtgccg taacgtgtag gcacgacagc atattagaca   1560
tcaatatagt cactcaggcc cgcaatcaac ccacaatgtt aaccgggtgc aaaataggaa   1620
agaacttttc gttctcaggt gaaattagag aaaaaccatg taattatgat atccaaccag   1680
aggaaatact acatttgcca cacgaatgtg gggagtggta tagtgaaata agccaccagg   1740
cggtcgacat gatcactaat gggttggagg cctctagaaa ttcagcagcc aaagtcttga   1800
gttggatagg gcgcaaattg gaaaggatag gaaagagagc acaagcaaaa tcaaaaacat   1860
ggtttggggc acaggcagct tccccctact gtgatgtcga tcgaaagatt ggctacatat   1920
ggtatacaaa aaattgtacc cctgcctgct tgcccaagaa cacaaaaatt gtcggccctg   1980
ggaagtttga caccaacgca gaggacggca agatactaca tgagatgggg ggccacttgt   2040
```

```
cggaggtact actactttct ttagtggtgc tgtccgactt cgcaccggaa acagccagcg   2100
caatgtacct aatcctacat ttttccatcc cacaaagtca cgttgacata atggaatgtg   2160
ataagaccca gttgaacctc acagtggagc ttacaacagc tgatgtaata ccaggatcag   2220
tctggaacct aggcaagtgg gtatgtataa gaccaaattg gtggccttat gagacaactg   2280
tggtgttggc atttgaagag gtgagccagg tggtgaagtt agtgttgagg gcactcagag   2340
atttgacacg catttggaac gctgcaacaa ctactgcttt cttaatatgc cttgttaaga   2400
tagtcagggg ccagatggta cagggcattc tgtggctact actgataaca ggggtacaag   2460
gggacttgca ttgcaaacct gaattctcat atgccatagc aagggatgaa agaattggtc   2520
aactgggggc tgaaggcctt actaccactt ggaaggatta ctcgcctgaa atgaaactgg   2580
aagacacaat ggtcatagct tggtgcaaag atggtaagtt tacgtacctc ccaaggtgca   2640
cgagagaaac cagatatctc gcgatcttgc atacaagggc cttaccgacc agtgtggtat   2700
tcaaaaaact tttgatgggc gaaagcaag aggatgtagt cgaaatggac gacaactttg   2760
aatttggact ctgcccatgt gatgccaaac ccatagtaag agggaaattc aatacaacgc   2820
tgctgaacgg accggccttc cagatggtat gccccatagg atggacaggg actgtaagct   2880
gtatgtcatt caatatggac accttagcca caaccgtgat acggacatat agaaggtcca   2940
aaccatttcc tcataggcaa ggctgtatca cccaaaagac tctgggggag gatctccata   3000
actgcatcct cggaggaaat tggacttgtg tgcctggaga cgtgctatta tacaaagggg   3060
gctctattga atcctgcaag tggtgtggtt atcaatttaa agagagcgag ggactaccac   3120
actaccccat tggcaagtgt agattagaga atgagactgg ttacagacta gtagacgata   3180
cctcttgtaa tagagaaggt gtggccatag taccacaagg gacattacgg tgcaagatag   3240
gaaaaactac tatacaggtc atagctatgg ataccaaact cggcctatg ccttgcagac   3300
catatgaaat aatatcaagt gaggggcctg tagaaaggac agcgtgtacc ttcaactaca   3360
ctaaaacatt aaaaaataag tattttgagc ccagagacag ctacttccag caatacatgc   3420
taaaaggaga gtatcaatac tggtttgacc tggaggtaac cgaccatcac cgggattact   3480
ttgccgagtc catattagtg gtggtggtag ccctcctggg tggcagatat gtactttggt   3540
tactagttac atacatggtc ttatcagaac agaaggcctc agggactcag tatggagcag   3600
gggaagtagt gatgatgggc aacttgctaa cccataatga cattgaagtg gtgacatact   3660
tcttgctgtt gtacctactg ctgagggaag agagcgtaaa gaagtgggtc ttacttttat   3720
accacatctt agtgtcacac ccaatcaaat ctgtaactgt gatcctattg atgattgggg   3780
atgtggtaaa ggcagactca gggggccaag ggtactttgg gcaaatagac ctctgtttta   3840
caatagttgt actaatcatc ataggtttaa tcatagccag gcgtgaccca actatagtgc   3900
cactagtaac aataatggca gcactgaggg tcactggatt gacctaccag cctggagttg   3960
acgtcgctat ggcagtcatg accataaccc tactgatggt tagctatgtg acagattact   4020
ttagatataa aagatggtta cagtgcgttc tcagcctggt gtcaggggtg ttcttgataa   4080
gaagcctaat gcacctaggt agaatagagg tgccagaggt aaccatccca aactggagac   4140
cactaacttt aatactgtta tatttgatct caacaacaat tgtaacaatg tggaaggttg   4200
acatcgctgg cttgttgttg caatgcctgc ctatcttatt actggccaca accttgtggg   4260
ccgacttctt aaccctcata ctgatcctgc ctacctatga attggttaaa ttatactacc   4320
tgaaaactgt taggactgat atagaaagaa gttggccagg ggggatagac tgtacaagag   4380
```

-continued

```
ttgactccat ctacgacatt gatgagagtg gagagggcgt atatctcttt ccatcaaggc   4440
agaaaggaca gaggagcttt tccatactct tgccccttgt caaagcaaca ctgataagtt   4500
gcgtcagcag taaatggcag ctaatataca tgagttacct aactttggac tttatgtact   4560
acatgcacag gaaagttata gaagagatat caggaggcac caacatgata tccaggttag   4620
tagcggcact catagagctg aactggtcca tggaagaaga ggagagcaaa ggcctaaaga   4680
agttttatct attatctgga aggttgagaa acctaataat aaaacataaa gtaagaaatg   4740
agaccgtggc ttcttggtac ggggaggagg aagtctacgg tatgccaaag atcatgacaa   4800
taatcaaggc cagtacgctg agtaagagca agcactgcat gatatgcact gtatgtgaga   4860
gccgagagtg gaaaggcggc acctgcccaa aatgtggacg ccatgggaag ccgataatgt   4920
gtgggatgtc gctagcggat tttgaagaaa gacactataa aagaatcttt ataagggaag   4980
gtaactttga gggtcctttc aggcaagaat acaatggctt tgtacaatat accgctaggg   5040
ggcaattact tgtgagaaac ttgcccgtac tggcaactaa agtaaaaatg ctcatggtag   5100
gcaaccttgg agaagaaatt ggtgatctgg aacatcttgg gtggatccta aggggggcctg   5160
ccgtgtgtaa gaagatcaca gagcacgaaa aatgccacat caatatactg gataaactaa   5220
ctgcattttt cgggatcatg ccgaggggga ctacacccag agccccggtg aggttcccta   5280
cgagcttact aaaagtgagg aggggcctgg agactggctg ggcttacaca caccaaggtg   5340
ggataagttc agtcgaccat gtaaccgccg gaaaagacct attggtctgt gacagcatgg   5400
gacggactag agtggtttgc caaagcaaca acaggttgac cgatgagaca gaatatggcg   5460
tcaagactga ctcaggatgc ccagacggtg ccagatgtta tgtgttaaat ccagaggctg   5520
tcaacatatc aggatccaag gggcagtcg tccacctcca aaagacaggt ggagaattca   5580
cgtgtgtcac cgcatcaggc acaccggcct ttttcgacct aaaaaacttg aaaggatggt   5640
caggattgcc tatattcgaa gcctccagcg ggagggtggt tggcagagtc aaagtaggga   5700
agaatgaaga gtctaaacct acaaaaataa tgagtggaat ccagaccgtc tcaaagaaca   5760
cagcagatct aactgagatg gtcaagaaga taaccagcat gaacagggga gacttcaagc   5820
agattacttt ggcaacaggg gcaggaaaaa ccacagaact cccaaaagca gttatagagg   5880
aaataggaag acacaagaga gtattagttc ttataccatt aagggcagcg gcagagtcag   5940
tttaccagta tatgagatta aaacacccaa gcatctcttt taacctaagg ataggggaca   6000
tgaaagaggg ggacatggca acggggataa cctatgcatc atacgggtac ttctgccaaa   6060
tgccccaacc aaagctcaga gctgctatgg tagaatactc atacatattc ttagatgaat   6120
accattgtgc cactcctgaa caactggcaa ttatcggaaa gatccacaga ttttcagaga   6180
gtataagagt cgtcgccatg actgccacgc cggcagggtc ggtgaccaca acaggtcaaa   6240
agcacccaat agaggaattc atagcccccg aggtaatgaa aggggaggat cttggtagtc   6300
agttccttga tatagcaggg ttaaaaatac cagtggatga gatgaaaggt aatatgttgg   6360
tttttgtacc cacgagaaac atggcagtag aggtggcaaa gaagctaaaa gctaagggct   6420
ataattctgg atactattac agtggagagg atccagccaa tctgagagtt gtaacatcgc   6480
agtctcccta tgtaatcgtg gccacaaatg ctattgaatc aggagtgaca ctaccagatt   6540
tggacacggt tgtagacacg ggctgaaat gtgaaaagag ggtgagggta tcatcaaaga   6600
tacccttcat cgtaacaggt cttaagagga tggccgtgac tgtgggtgag caggctcagc   6660
gtaggggcag agtaggtaga atgaaacccg ggagatatta tagaagccag gaaacagcaa   6720
ccgggtcaaa ggactaccac tatgacctct tgcaggcaca aagatacggg attgaggatg   6780
```

-continued

```
gaatcaacgt aacgaagtcc tttagggaga tgaattacga ttggagccta tacgaggagg   6840
acagcctact aataacccag ttggaaatac taaataatct actcatctca gaagacttgc   6900
cagccgctgt taagaatata atggccagga cagatcaccc agagccaatc caacttgcat   6960
acaacagcta tgaagtccag gtcccggtcc tgttcccaaa aataaggaat ggagaagtca   7020
cagacaccta cgaaaattac tcgtttctaa acgccagaaa gttaggggag gatgtacccg   7080
tgtatatcta tgccactgaa gatgaggatc tggcagttga cctcttaggg ctagactggc   7140
cagatcctgg gaaccagcag gtagtggaga ctggcaaagc actgaagcaa gtgaccgggt   7200
tgtcctcggc tgaaaatgcc ctactagtgg ctttatttgg gtacgtaggt tatcaggctc   7260
tctcaaagag gcatgtccca atgataacag acatatatac catcgaggac cagagactag   7320
aagacaccac ccacctccag tatgcaccca acgccataaa aaccgaaggg acagagactg   7380
aactgaaaga actggcgtcg ggtgacgtgg aaaaaatcat gggagtcatt tcagattatg   7440
cagccggggg actggagttt gtgaaatccc aagcagaaaa gataaaaaca gcacctttgt   7500
ttaaagaaaa cgtagaagct gcaaaagggt acgtccaaaa attcattgac tcattaattg   7560
aaaataaaga tgcaataatc agatatggtt tgtggggaac acacactgca ctatacaaaa   7620
gcatagctgc aagactggga cacgaaacag cgtttgccac actggtgtta aaatggctag   7680
cttttggagg ggaatcagtg ccagaccaca tcaagcagac ggcagttgat ttagtggtct   7740
attatgtgat gaataagcct tccttcccag gcgacaccga aacacagcaa gaagggaggc   7800
gattcgtcgc tagcctgttc atctccgcac tggcaaccta cacatacaaa acttggaatt   7860
accacaatct ctctaaagtg gtggaaccag ccttggctta cctcccctat gctaccagcg   7920
cattaaaaat gttcacccca acgcggctag agagcgtggt gatactgagc accacgatat   7980
acaaaacata cctctccata aggaagggga agagtgatgg attgctgggc acggggatca   8040
gtgcagccat ggaaatcctg tcacaaaacc cagtgtcggt gggtatatct gtgatgttgg   8100
gggtaggggc cattgctgcg cacaacgcta ttgagtccag tgaacagaaa aggaccctac   8160
ttatgaaggt gttcgtaaag aacttcttgg atcaggctgc aacggatgag ctggtaaaag   8220
aaaacccaga gaaaattata atggccttat ttgaagcagt ccagacaatt ggtaaccccc   8280
tgagactaat ataccacctg tatggggttt actacaaagg ttgggaggcc aaggaactat   8340
ctgagaggac agcaggcaga aacttattca cattgataat gtttgaagcc ttcgagttat   8400
tagggatgga ctcagaagga aaaataagga acctgtccgg aaattacatc ttggatctga   8460
tatacggcct acacaagcag atcaacagag ggctgaagaa aatagtactg gggtgggctc   8520
ctgcaccctt tagttgtgac tggaccccta gcgacgagag gatcagattg ccaacagaca   8580
actatttgag ggtagaaacc aggtgcccat gtggttatga gatgaaagcg ttcaaaaatg   8640
taggtggcaa gcttaccaaa gtggaggaga gcgggccttt cctatgtaga aacagacctg   8700
gtaggggacc agtcaactac agagtcacca agtattacga tgacaacctc agagagataa   8760
aaccggtagc aaagttggaa ggacaggtgg agcactacta taaaggggtc acagcaaaaa   8820
ttgactacag taaaggaaaa acgctcttgg ctactgacaa gtgggaggtg gaacatggtg   8880
tcatgaccag gttagctaag agatatactg ggttgggtt caatggtgca tacttaggtg    8940
atgagcccaa tcaccgtgat ctagtggaga ggaactgtgc gactataacc aaaaacacag   9000
tacagtttct aaaaatgaag aaggggtgtg cattcaccta tgacctgacc atctccaatc   9060
tgaccaggct tattgaacta gtacacagga acaatcttga agagaaggaa atacccaccg   9120
```

```
ttacagtcac tacatggcta gcttacacct tcgtgaatga agacgtaggg actataaaac   9180
cagtactagg agagagggta atccccgacc ctgtagttga tgtcaactta caaccagagg   9240
tccaagtgga tacatcagag gtcgggatca caataattgg aagggaaacc ctgatgacaa   9300
cgggggtgac acctgtattg gaaaaagtag agcctgacgc tagcaacaac caaagctcag   9360
tgaagattgg gttggataag ggtaattacc cagggcctgg aatacagaca catacactaa   9420
cagaagaaat acacgacagg gatgcaagac ccttcatcat gatcctgggc tcaaagaatt   9480
ccatgtcaaa tagggcaaag actgctagaa acataaatct gtacacagga aatgacccca   9540
gggaaataag agacttgatg gctgcagggc gcatgttagt agtagcactg agggatgtcg   9600
accctgagct ttctgaaatg gtcgacttca aggggacctt cttagatagg gaggccctgg   9660
aggctctaag tctcgggcaa cctaaaccta agcaggtcac caaggcagct attagggatt   9720
tgattgaaca ggaaaaacag gtggagatcc ctaactggtt tacatcagat gacccagtat   9780
ttttggaagt ggccataaga aatgataagt actacttagt aggagatgtt ggagaggtaa   9840
aagatcaagc taaaacactt ggggccacgg atcagacaag aattgtaaag gaggtaggct   9900
caaggacgta taccatgaag ctatctagtt ggttcctcca agcatcaaaa aaacagataa   9960
gtttaactcc actgtttgag gaattgttgt tacggtgccc acctgcaact aagagcaata  10020
aggggcacat ggcatcagct taccaattgg cacagggtaa ctgggagccc ctcggttgcg  10080
gggtgcacct aggtaccata ccagctagaa gggtgaagat acacccatat gaagcttacc  10140
tgaggttgaa agattttta gaagaagaag agaagaaacc tagggttaag gatacagtaa  10200
taagagagca caacaaatgg atacttaaaa aaataaggtt tcaaggaaac ctcaacacca  10260
agaaaatgct caaccccggg aaactatctg aacagttgga cagggagggg cgcaaaagga  10320
acatctacaa ccaccagatt ggtaccataa tgtcaagtgc aggcataagg ctggagaaat  10380
tgccaatagt aagggcccaa accgacacta aaacctttca tgaggcaata agagataaga  10440
tagacaagag tgagaaccgg caaaatccag aattgcacaa caaattgttg gagatttttc  10500
acacaatagc ccaacccgcc ctgaaacaca cttacggtga ggtgacgtgg gagcaacttg  10560
aggcagggat aaataaaaaa ggggcagcag gctttctgga gaagaagaac atcggggaag  10620
tattggattc agaaaaacac ctggtggaac aattggtcag ggatctgaag gccgggagaa  10680
agataaaata ttatgaaact gcaataccaa aaaatgagaa aagagatgtc agcgatgact  10740
ggcaggcagg ggacctggtg gatgagaaga ggccaagagt tattcaatac cctgaagcca  10800
agacaaggct agccatcact aaggtcatgt ataactgggt gaaacagcag cccgttgtga  10860
ttccaggata tgaaggaaag acccctttgt tcaacatctt tgataaagtg agaaaggaat  10920
gggacttgtt caatgagcca gtggccgtaa gttttgacac caaagcctgg gacacacaag  10980
tgactagtag ggatctgcaa cttatcggag aaatccagaa atattactat aggaaggagt  11040
ggcacaagtt cattgacacc atcaccgacc acatgacaga agtgccagtt ataacagcag  11100
atggtgaagt atatataaga aatgggcaga gaggtagtgg ccaaccagac acaagtgcag  11160
gcaacagcat gttaaatgtc ctaacaatga tgtacgcttt ctgcgaaagc acaggggtcc  11220
cgtacaagag tttcaacagg gtggcaagga tccatgtctg tggggatgat ggcttcttaa  11280
taactgaaaa agggttaggg ctgaaatttg ctaacaaagg gatgcagatt cttcacgaag  11340
caggcaaacc tcagaagata acggaagggg aaaagatgaa agttgcctat agatttgagg  11400
acatagagtt ctgttcccat accccagtcc ctgttaggtg gtccgacaat accagtagtc  11460
acatggccgg gagagacacc gctgtgatac tatcaaagat ggctacaaga ttggattcaa  11520
```

atggagagag gggtaccaca gcatatgaaa aagcggtagc cttcagtttc ttgctgatgt 11580
attcctggaa cccgcttgtt aggaggattt gcctgttggt actttcgcaa cagccagaga 11640
cagacccatc caaacaggcc acttattatt acaaaggtga tccaataggg gcctataaag 11700
atgtgatagg tcggaatcta agtgaactaa agagaacagg cttcgagaaa ttggcaaatc 11760
taaacctaag cctgtccaca ttagggatct ggactaagca cacaagcaaa agaataatta 11820
atgactgtgt tgccattggg aaagaagaag gcaactggct agttaacgcc gacaggctga 11880
tatccagcaa aactggccac ttatacatac ctgataaggg ctttacatta caaggaaagc 11940
attatgagca actacagcta agaacagaga caaaaccggt catgggggtc gggactgaga 12000
gatacaagtt gggtcccata gtcaatctgc tgctgagaag gttgaaagtt ctgctcatga 12060
cggccgtcgg tgccagcagc tgagacaagt gtatatattg taaataaatt aacccatgta 12120
catattgtat ataaatatag ttgggatcgt ccacctcaag aagacgacac acccaacacg 12180
cacagctaaa cagtagttaa gattatctac ctcaagataa cactacattt aatgcacaca 12240
gcactttagc tgtatgagga tacgcccgac gtctacagtt ggactaggga agacctctaa 12300
cagcccc 12307

<210> SEQ ID NO 32
<211> LENGTH: 12663
<212> TYPE: DNA
<213> ORGANISM: Artificial Sequence
<220> FEATURE:
<223> OTHER INFORMATION: Erns chimeric virus
<220> FEATURE:
<221> NAME/KEY: misc_feature
<223> OTHER INFORMATION: BVDV Type 2

<400> SEQUENCE: 32
gtatacgaga ttagctaaag tactcgtata cggattggac gtcaacaaat ttttttaatt 60
ggcaacgtag ggaactttcc cctcagcgaa ggccgaaaag aggctagcca tgcccttagt 120
aggactagca aaaatagggg actagcggta gcagtgagtt cattggatgg ccgaacccct 180
gagtacaggg gagtcgtcaa tggttcgaca ctccattggt tgaggagtct cgagatgcca 240
tgtggacgag ggcatgccca cggcacatct taacccatgc gggggttgca tgggtgaaag 300
cgctattcat ggcgttatgg acacagcctg atagggtgta gcagagacct gctattccgc 360
tagtaaaaac tctgctgtac atggcacatg gagttgtttt caaatgaact tttatacaaa 420
acatataaac aaaaaccagc aggcgtcgtg gaacctgttt acgacgtcaa cgggcgtcca 480
ctgtttggag agagcagtga cttgcacccg cagtccacgc taaaactacc acaccaacga 540
ggtagtgcca acatcctgac caatgctagg tccctaccgc ggaaaggtga ctgccggaga 600
ggtaatgtgt atggagcggt gagtggcatc tatatcaagc caggaccgat ctactaccag 660
gattatgcgg agcctgtcta ccatagagcc ccattagaac tatgtaggga ggcaagtatg 720
tgcgaaacaa ctaggagagt tggcagagtg accggtagtg atgggaaatt atatcatatc 780
tacatctgca tagatgggtg tatcctcctg aagagggcga ctaggaatca accagaagtc 840
ctaaaatggg tatacaacag attagattgt cctttatggg tcactagctg ctccgatgaa 900
gggagtaaga gtgctacaag taagaagcag cctaagccag ataggataga aaaaggcaag 960
atgaaaatag ccccaaaaga gacagaaaaa gattgcaaaa ccagaccccc cgacgcgact 1020
atagtagtag aaggggttaa gtaccaggtg aagaaaaaag gaaaggtaag gggaaaaaat 1080
actcaagatg ggttgtatca caacaagaat aagcccccctg aatcaagaaa gaaattggaa 1140

-continued

```
aaggcactac tagcttgggc catcttggca gcggttctgc ttcagctggt aacaggagtg   1200
aatataactc agtggaacct ggctgacgaa ggcaccgaag gcgtacatag ggtcatgttt   1260
gagagaggga taaatagaag tttacatggc atatggcccc aacagatatg ccacggaatc   1320
ccaagctaca accccaccaa cagagagctc tcgatgattg tcggaatggt tgatgcaagc   1380
attagaacaa attatacctg ctgtaatcta cagagacacg aatggaacaa acatggctgg   1440
tgcaattggt acaacatcat accatggatt aaggtgatga actacagcca gaggaacctc   1500
actgaaggca catatggcaa agagtgtgcc gtaacgtgta ggcacgacag catattagac   1560
atcaatatag tcactcaggc ccgcaatcaa cccacaatgt taaccgggtg caaaatagga   1620
aagaactttt cgttctcagg tgaaattaga gaaaaaccat gtaattatga tatccaacca   1680
gaggaaatac tacatttgcc acacgaatgt ggggagtggt atagtgaaat aagccaccag   1740
gcggtcgaca tgatcactaa tgggttggag gcctctagaa attcagcagc caaagtcttg   1800
agttggatag ggcgcaaatt ggaaaggata ggaaagagag cacaagcaaa atcaaaaaca   1860
tggtttgggg cacaggcagc aagtccatac tgtaaagtgg agaggaagat cggttacatc   1920
tggtatacaa aaaactgcac tccagcttgc cttccaagaa acactaaaat aataggcccc   1980
gggaagtttg ataccaacgc cgaagatgga aaaatactcc atgagatggg ggggcacctc   2040
tcagaatttg tcctattgtc tttggtggtt ctgtctgact ttgccccaga aaccgcgagt   2100
gccatctact tggttctaca ttttgcgatc ccgcaaaacc acgttgatgt agacacatgc   2160
gacaagaacc agctgaattt aacggtcgca actacagtag cagaggtcat accagggaca   2220
gtgtggaacc tagggaagta tgtctgcata agaccagact ggtggccata tgagacgacg   2280
acagtcttcg tcttagagga agcagggcaa gtaatcaaat tggggctaag ggccatcaga   2340
gacttaacta ggatatggaa tgctgccacc accacagctt tcctaatctt tttagtgaaa   2400
gcactaaggg gacaactaat ccaagggcta ttgtggctga tgctaataac aggagcacag   2460
ggtttccctg aatgcaaaga gggcttccaa tatgccatat ctaaagacag aaaaatgggg   2520
ttactgggac cagagagctt aactacaaca tggcacctcc ccaccaaaaa aatagtggac   2580
tccatggtaa gtgtatggtg tgaaggaaaa gacttaaaaa tattaaaaac gtgcacaaag   2640
gaagagaggt acctagtggc tgtgcacgag agagccttat caaccagtgc cgagtttatg   2700
cagatcagtg atgggacaat aggcccagac gtgatagata tgcctgatga ctttgagttt   2760
ggactctgcc cttgtgactc aaaaccagtg ataaagggca aatttaatgc cagcttactg   2820
aatggaccag ctttccagat ggtatgccca caggggtgga ctggtacagt agaatgcacc   2880
ctagtgaacc aagacacctt ggacacaact gtcattagga catatagaag aactacccca   2940
tttcagcgga gaaaatggtg tacctatgaa aaaataatag gggaagatat ccatgaatgc   3000
attctaggtg gaaactggac atgcataacc ggtggccaca gcgggttgaa agacggacct   3060
atcaagaagt gtaagtggtg tggctatgac ttcgtcaact cagagggact accacactac   3120
ccaataggca agtgcatgct catcaatgag agtgggtaca ggtatgtaga tgacacctct   3180
tgcgataggg gtggtgtagc catagttcca actggcaccg taaagtgtag aataggtaac   3240
gtcacggtgc aagttatcgc tactaacaat gatctgggac ccatgccttg cagcccagct   3300
gaagtgatag caagtgaagg accagtggaa aagactgcat gcacattcaa ctattcaagg   3360
actctaccta ataagtatta tgagccaagg gaccggtact tccaacaata catgttaaaa   3420
ggggggtggc aatattggtt cgacctggat tctgtagacc accacaaaga ctacttctca   3480
```

-continued

```
gagttcataa tcatagcagt ggtcgccttg ttgggtggta agtacgtact atggctcttg   3540
ataacataca caatactgtc tgagcagatg gctatgggcg ctggagtgag tactgaagag   3600
atagtcatga taggcaactt gctgacacac agtgatattg aggttgtggt ctatttcctt   3660
cttctgtact taatagttaa agaggaactg gtgaggaaat gggttatact ggtataccac   3720
atccttgtag ctaaccctat gaaaacaact ggggtcatct tactaatgct agggggagtg   3780
gtgaaggcca gcagaatcaa tgctgatgac caaagtgcta tggacccatg ctttcttctc   3840
gtgacaggtg tagtggctgt tttgatgatc gctagaagag aacctgccac cttaccactg   3900
attgtagcat tgctagcaat aagaacatca ggattcctac tgtccgctag cattgatgta   3960
actgtagcag tagtattaat tgtacttttg ctggctagct acgtaacaga ctactttaga   4020
tataaaaagt ggcttcaatt ctcatttagt ctgatagctg gtatctttat tataaggagc   4080
ttgaaacata tcaaccagat ggaggtacca gaaatatcta tgccaagttg gagacctcta   4140
gctcttgtct tcttctatat aacatctaca gcaataacca ctaattggga cattgactta   4200
gcaggcttcc tgctgcaatg ggcgccagca gtgatcatga tggctaccat gtgggcagac   4260
tttttgactc tgatcatagt cctgcccagt tacgagttat ctaagcttta cttcctaaag   4320
aacgtcagga cagacgtgga aaagaactgg ctcggcaagg tgaaatacag acagatcagt   4380
tcagtttatg acatctgtga cagtgaggaa gcagtgtacc tatttccatc aaggcataag   4440
agtggaagca ggccagattt catattaccc tttttgaaag ccgtgttaat aagctgcatc   4500
agcagccaat ggcaaatggt ttacatttct tacctaatac tggaaatcac atactatatg   4560
cacaggaaaa tcatagatga ggtgtcagga ggagcaaatt ttctatcaag acttatagca   4620
gccatcatag aattaaattg ggccatagat gatgaggaat gtaaagggct gaagaaactg   4680
tatctcttgt cagggagagt gaagaattta atagttaaac ataaggtaag aaatgaagcc   4740
gtccacagat ggtttggtga ggaggaaata tatggggcac ccaaggtgat caccatcata   4800
aaagctagta ccctaagtaa aaacaggcac tgcataatct gcacgatctg tgaagggaaa   4860
gaatggaacg gagccaactg cccaaagtgt ggaagacaag gaaagcccat aacatgtgga   4920
atgacactcg cagactttga ggagaaacat tacaaaaaga tatttataag agaaggacgc   4980
caagaagcaa tgaatacgat gatgtgcagc cgatgccagg gaaagcatag gaggtttgaa   5040
acggaccggg aacctaagag tgccagatac tgtgctgagt gtaataggct gcatcctgct   5100
gaggaaggtg acttttgggc agagtcaagc atgttgggcc tcaaaatcac ctactttgcg   5160
ctgatggatg gaaaggtgta tgatatcaca gagtgggctg gatgccagcg tgtgggaatc   5220
tccccagata cccacagagt cccttgtcac atctcatttg gttcacggat gccaggcacc   5280
agtgggcggc agagagctac tccagatgcc cctcctgctg accttcagga tttcttgagc   5340
cggatctttc aagtaccccc aggccagatg tccagggaag agtataaggg ttacgtccaa   5400
tacacagcca gaggacaact ctttctgagg aacctgccaa ttctagcgac gaagatgaag   5460
ctattaatgg tggggaacct cggcgcagaa gttggcgacc tggaacatct aggatgggta   5520
ctgagagggc cagccgtgtg caaaaaaatt accaaccatg agaagtgcca cgtaaacatc   5580
atggataagc taactgcatt ttttggaatc atgcctagag gcacaacccc tagggcacct   5640
gtgaggttcc ccacagcact attgaaagtg agaagggggc tagagacggg atgggcttac   5700
acacaccaag gagggatcag ctcggtagac catgtcacag ccggaaagga tttactggtg   5760
tgtgacagta tgggcaggac cagggttgtc tgtcatagta acaataagat gactgacgag   5820
actgagtatg gcatcaagac cgactcaggg tgccccgaag gcgcgaggtg ttacgtgcta   5880
```

aacccagaag ctgttaacat ttctggcaca aaaggagcta tggtacacct ccagaaaact 5940 ggggggagt tcacatgtgt cactgcctca gggaccccgg ctttcttcga tctaaaaaat 6000
ctaaaaggct ggtccgggct gccaattttt gaagcatcca gtggcagggt ggttggtagg 6060
gtgaaagtcg gcaagaatga ggattccaag cccaccaaac taatgagcgg aatccagaca 6120
gtgtctaaga gccagacgga cctagcggac atcgtaaaga aattgactag tatgaacaga 6180
ggagagttca aacagataac attagccact ggggcaggaa aaactacgga actgccaagg 6240
tccgttatag aggagatagg gaggcacaaa agggtcttag tcctgatacc attgagagcg 6300
gcagcagagt cagtgtatca gtatatgaga gtgaagtacc caagtatatc tttcaatttg 6360
agaataggag atatgaagga aggtgatatg gccaccggta tcacttacgc ctcatatggg 6420
tacttttgtc agcttcctca gcccaaactg agagctgcca tggtagagta ttcatatata 6480
ttcttagatg agtaccactg tgctacaccc gagcaattag caataattgg aaagatacac 6540
aggtttgctg aaaatcttag agtggtagca atgacagcaa ccccagctgg aacggtcaca 6600
acgactggtc agaaacaccc tatagaggag ttcatagccc cagaggtgat gaagggtgaa 6660
gatctaggta gtgaatactt ggatattgca gggttgaaga taccgactga agagatgaaa 6720
ggcaacatgc tcgtgttcgt gccaactagg aacatggcag tagaaacagc taagaaattg 6780
aaggcaaaag ggtacaactc cggatactat tacagtgggg agaacccaga aaacttgagg 6840
gtggtgacct cacaatcccc gtatgtggta gtagccacca atgccataga gtcaggtgtg 6900
acattaccag acttagacac agttgtagac actggactaa aatgtgagaa gagggtgagg 6960
atatcttcaa aaatgccctt cattgtaaca ggacttaaga gaatggcagt cacaatagga 7020
gagcaagccc agcgcagggg gagagtagga agagtcaagc caggtaggta ctataggagt 7080
caagaaacag cttcagggtc aaaagattac cattacgacc tactacaagc ccagaggtac 7140
ggaatagaag atggaattaa tgtaacaaag tcattcaggg agatgaacta tgattggagc 7200
ctttatgaag aggacagctt gatgataact caactcgagg tccttaacaa cctccttata 7260
tcagaagacc tgcctgccgc agtgaagaac atcatggccc ggaccgatca cccagaaccc 7320
atacaactgg cctataacag ttatgaaaac caagttccag tgctgttccc aaagatcaaa 7380
aatggtgagg tgacagacag ttatgagaat tacacatacc tcaatgcaag aaaactagga 7440
gaggacgtgc cggcgtatgt gtacgccacg gaggatgagg atctagcagt ggatcttctg 7500
ggtatggatt ggccggaccc aggcaaccaa caggtggtag agacagggag ggcattaaag 7560
caagtaactg gcttatccac agcagaaaat gccctcttga tagccttatt cggttacgtc 7620
gggtaccaga cgctttcaaa aaggcacata cccatgatta ctgacatcta tacacttgaa 7680
gaccacagac ttgaggacac aacccacctc cagtttgccc caaacgctat aaggaccgac 7740
ggcaaggact cagagttgaa agaattagct gtgggagacc ttgataaata tgtggacgca 7800
ctggtagact actccaaaca agggatgaaa tttatcaaag tccaagctga aaaggtcaga 7860
gactcccagt ctacaaagga aggcttgcaa aatattaagg agtatgtgga taagtttata 7920
caatcactaa cagagaataa ggaggagatc atcaggtatg gactatgggg agttcacaca 7980
gcactctaca aaagcttggc agcgagactg gggcatgaaa cagcttttgc aactttagtg 8040
gtaaaatggc tggcttttgg gggcgaaacg gtatctgctc acatcaagca agtagcagtt 8100
gatctagtag tatactatat catcaacaaa ccatcctttc ctggagatac agagacccaa 8160
caagagggga ggaggtttgt ggctagtctt tttatatctg cactagcaac atacacatat 8220

-continued

```
aaaacctgga attacaacaa tctgcaacgg gttgtcgaac ctgccttagc ttacctccca   8280
tatgctacaa gtgccttgaa gttgttcgca cccacaagat tagagagtgt ggtcatactc   8340
agttctacaa tttacaagac atacctctct ataaggaagg gtaagagcga cggcttgtta   8400
ggtacaggca taagtgcagc catggagatc ctaaaccaaa acccaatctc agtaggtata   8460
tctgtgatgc tgggggtagg tgccatcgcc gcccataatg caatagaatc tagtgaacag   8520
aaaagaactt tgctgatgaa ggtctttgta aaaaattttt tggaccaagc agcgacagat   8580
gagctagtca aagagaaccc tgaaaaaata atcatggctc tatttgaagc agtccagacc   8640
ataggaaacc ccctaagact catctaccat ctgtacgggg tgtactataa ggggtgggaa   8700
gcaaaagaac tcgcagagaa aactgctggc cgcaacttat tcacattgat tatgtttgaa   8760
gcctttgagc ttttaggtat ggactcagaa ggaaagataa gaaacttgtc aggcaactac   8820
atactggact taatcttcaa tttgcataat aaattaaaca agggtctcaa aaaactagtc   8880
cttgggtggg ctccagcacc tttcagctgt gattggacac caagtgatga gaggataagc   8940
ttaccccata acaactactt aagggtagaa accaggtgtc cttgtggcta tgagatgaag   9000
gcaataaaaa atgttgctgg taaattgaca aaagttgaag aaaaggggcc cttcctatgc   9060
aggaatagat tagggagagg acctccaaac ttcaaagtaa caaagttcta tgatgatgac   9120
ttgaaagaag tcaagccagt agctaggcta gaaggccagg tggacctcta ttacaaggga   9180
gtaacagcaa agttagacta caacaatggg aaagtactgt tagctaccaa caagtgggag   9240
gtggaccacg ctttcctgac cagattagta aagaagcaca cagggatagg ttttaaaggt   9300
gcatatttgg gtgacagacc agaccatcaa gatcttgtcg atagagattg tgcaactata   9360
acgaagaact cagtacagtt cctaaaaatg aagaaaggtt gcgctttcac atatgaccta   9420
acaatctcta accttgtcag gcttattgaa ctagtccata agaacaattt acaagaaaga   9480
gagatcccca ccgtgacagt aactacttgg cttgcatatt cttttgtcaa tgaagacctg   9540
gggactatca agcctgtatt gggggagaaa gtcatcccag aaccccccga ggagttgagt   9600
ctccaaccca ctgtgggact agtcaccact gagacagcaa taaccataac aggggaggct   9660
gaagtgatga cgacagggat cacaccagtg gtagagatga aagaagaacc tcagctggac   9720
caccagtcaa ctaccctaaa ggtagggtta aaggaagggg aatatccagg gccaggagtt   9780
aaccctaacc atttagtaga ggtgatagat gagaaagatg acaggccttt tgtcctaatt   9840
atcggtaaca aaggttctac ctcgaacaga gcaagaacgg ccaagaatat acggctgtac   9900
aaaggaaaca acccaagaga gatcagggat ctgatgagcc aaggaagaat attaacggtt   9960
gctctaaaag agttggaccc ggaattaaaa gaattagtag attacaaggg gacctttctc  10020
aatagggaag ctttagaagc cctaagctta ggtaagccaa ttaagaggaa aaccacagca  10080
gcaatgatca ggaggttaat agagccagag gttgaggagg aactaccaga ttggttccaa  10140
gcggaagaac ccctattttt ggaagcaaaa atacagaatg acttatacca cctaattggc  10200
agtgttgata gtataaaaag caaagcaaag gaattagggg ccacagataa cacaaagata  10260
gtgaaggaag tcggggctag gacctatacg atgaaattga gtagctggag cacacaagtt  10320
actaaaaaac agatgagttt agcccctctc tttgaagagc tgttattaaa gtgccctcca  10380
tgtagtaaaa tttcaaaggg acatatggtg tcagcatacc aactggctca aggaaactgg  10440
gaacccctcg ggtgtggggt ctatatggga accataccag ctaggcgtct caagatccac  10500
ccttatgagg cttaccttaa actcaaagag ctgctggaag ttgaatcttc gaggatcacc  10560
gcaaaagaat ccatcataag agaacataac acctggattc tgcggaaagt gagacatgag  10620
```

-continued

```
gggaacctaa gaactaaatc aatgattaac cctgggaaaa tatcagatca gctatgcaga  10680
gacggacaca aaagaaacat atataataag atcataggct caacaatggc ctctgctggt  10740
attaggctgg agaaactgcc agtagtccga gcccaaactg acacaaccag tttccaccaa  10800
gccataagag aaaaaattga taaaccagaa aacaagcaga cccctgaatt gcatgaagaa  10860
ctaatgaagg ttttcgactg cttaaagatc ccagagctga aggaatcgta tgatgaagtt  10920
tcatgggaac aattagaagc aggaataaac cgtaagggtg cagcaggtta tctagagagt  10980
aagaacatag gggaagtgct agacacagag aaacacatag tagagcagct gatcaaggat  11040
ctgaggaagg ggaagaagat taagtactat gaaacagcca ttcccaagaa tgagaagaga  11100
gacgtcagcg acgactggga agccggagac ttcgttgatg aaaagaaacc aagagtaatc  11160
cagtacccgg acgccaaggt gagactggca attacaaaaa tgatgtacaa atgggtaaag  11220
caaaaaccag tggtgatacc cggctatgaa ggaaaaacac cactatttga catattcaac  11280
aaagtgaaga aggaatggga ttcattccag gaccccgtag cagtgagctt tgacaccaaa  11340
gcgtgggata cacaagtcac cagtagagac ctaatgttga taagggatat ccagaaatat  11400
tatttcaaga gaagtacaca caaattttta gatacaataa cagaacacat ggtagaagta  11460
cctgtcatta cagcagacgg tgaagtttac ataaggaatg gtcagagggg tagtggccaa  11520
cccgacacaa gtgctggtaa tagtatgttg aatgtcctaa ccatgatata tgctttctgt  11580
aaaagtacag gcatacctta caggggattc agcagagtgg caagaatcca tgtgtgtggt  11640
gatgatggct ttctgataac agaaagagga ctggggctga aattctctga gaagggtatg  11700
cagatattac atgaggccgg gaagccccag aaaataactg aaggggacag aatgaaagtg  11760
gcatacagat ttgaggacat cgagttttgt tcccatacac ccgtaccagt cagatgggca  11820
gataacacca gtagttacat ggcagggagg agcacagcca ctatactagc taagatggca  11880
accaggttgg attccagcgg agagaggggt agcacagctt atgagaaggc cgtagccttc  11940
agcttccttt tgatgtactc atggaatccc gtagttagaa ggatctgctt actggtgttg  12000
tcacagtttc cagaaatatc ccatccaaaa aacacaatat actactacca aggggatccc  12060
atagctgcgt acagagaagt gataggtaaa cagctgtgtg aactgaaaag aacaggattt  12120
gagaagctgg ctggtctgaa tttgagtatg accactctag gcatctggac aaaacattct  12180
agtaaaagac taatccaaga ctgtgtagag ataggtaaga gagaaggtaa ctggttagtt  12240
aatgctgaca gactgattgc aggaaagact gggaagtttt acatcccaag cactggtgtc  12300
actctgttgg gaaaacatta tgaggaaatt aacttaaagc aaaaggcggc acaaccgccg  12360
atagaggggg ttgacagata taagttgggc cccatagtta atgtaatctt gagaaggctg  12420
agggtgatgc tgatgacagt tgccagcgga agctggtaaa tccgtccgga gcatcgtgcc  12480
ctcgctcaag gttttaattg taaatattgt aaatagacag ctaagatatt tattgtagtt  12540
ggatagtaat gtagtgatag tagatacccc aatttaacac tacctccaat gcactaagca  12600
ctttagctgt gtgaggttaa ctcgacgtcc acggttggac tagaggatgc ctctgacagc  12660
ccc                                                                12663
```

CHIMERIC PESTIVIRUSES

CROSS-REFERENCE TO RELATED APPLICATIONS

This application claims benefit of priority under 35 U.S.C. 119(e) to U.S. Provisional Application Nos. 61/119,594 filed Dec. 3, 2008, and 61/173,363 filed Apr. 28, 2009, each of which is herein incorporated in its entirety by reference.

FIELD OF THE INVENTION

The present invention relates to novel chimeric pestiviruses and their use in immunogenic compositions and vaccines. It also relates to methods and kits for treating or preventing the spread of bovine viral diarrhea virus infection. The present invention further relates to the use of the chimeric pestiviruses in methods and kits for differentiating between vaccinated animals and animals infected with a wild-type virus.

BACKGROUND

Pestiviruses, including bovine viral diarrhea virus (BVD virus, or BVDV), have been isolated from several species of animals, both domestic and wild. Identified hosts for BVDV include buffalo, antelope, reindeer and various deer species, while unique pestivirus species have been identified in giraffes and pronghorn antelope. BVDV is a small RNA virus of the family Flaviviridae. It is closely related to other pestiviruses which are the causative agents of border disease in sheep and classical swine fever in pigs. Recently a divergent pestivirus named Bungowannah pestivirus was identified as an etiologic agent of fetal infection of piglets in Australia.

Disease caused by BVDV particularly in cattle is widespread, and can be economically devastating. BVDV infection in cattle can result in breeding problems, and can cause abortions or premature births. BVDV is capable of crossing the placenta of pregnant cattle, and may result in the birth of persistently infected (PI) calves that are immunotolerant to the virus and persistently viremic for the rest of their lives. Infected cattle can also exhibit "mucosal disease", characterized by elevated temperature, diarrhea, coughing and ulcerations of the alimentary mucosa. These persistently infected animals provide a source for dissemination of virus within the herd for further outbreaks of mucosal disease and are highly predisposed to infection with microorganisms responsible for causing enteric diseases or pneumonia.

BVDV is classified into one of two biotypes. Those of the "cp" biotype induce a cytopathic effect on cultured cells, whereas viruses of non-cytopathic, or "ncp", biotype do not. In addition, two major genotypes (type 1 and 2) are recognized, both of which have been shown to cause a variety of clinical syndromes.

BVDV virions are 40 to 60 nm in diameter. The nucleocapsid of BVDV consists of a single molecule of RNA and the capsid protein C. The nucleocapsid is surrounded by a lipid membrane with two glycoproteins anchored in it, E1 and E2. A third glycoprotein, $E^{rns}$, is loosely associated to the envelope. The genome of BVDV is approximately 12.5 kb in length, and contains a single open reading frame located between the 5' and 3' non-translated regions (NTRs). A polyprotein of approximately 438 kD is translated from this open reading frame, and is processed by cellular and viral proteases into at least eleven viral structural and nonstructural (NS) proteins (Tautz, et al., *J. Virol.* 71:5415-5422 (1997); Xu, et al, *J. Virol.* 71:5312-5322 (1997); Elbers, at al., *J. Virol.* 70:4131-4135 (1996); and Wiskerchen, et al., *Virology* 184:341-350 (1991)). The genomic order of BVDV is p20/$N^{pro}$, p14/C, gp48/$E^{rns}$, gp25/E1, gp53/E2, p54/NS2, p80/NS3, p10/NS4A, p32/NS4B, p58/NS5A and p75/NS5B. The three envelope proteins, gp48/$E^{rns}$, gp25/E1 and gp53/E2, are heavily glycosylated. $E^{rns}$ (formerly referred to as E0 or gp48) forms homodimers, covalently linked by disulfides. The absence of a hydrophobic membrane anchor region suggests that $E^{rns}$ is loosely associated with the envelope. $E^{rns}$ induces high antibody titers in infected cattle, but the antisera has limited virus-neutralizing activity.

Among the BVDV vaccines currently available are those which contain chemically-inactivated wild-type virus. These vaccines typically require the administration of multiple doses, and result in a short-lived immune response; they also do not protect against fetal transmission of the virus. In sheep, a subunit vaccine based on a purified E2 protein has been reported. Although this vaccine appears to protect fetuses from becoming infected, protection is limited to only the homologous strain of virus, and there is no correlation between antibody titers and protection.

Modified live (ML) BVDV vaccines have been produced using virus that has been attenuated by repeated passaging in bovine or porcine cells, or by chemically-induced mutations that confer a temperature-sensitive phenotype on the virus. A single dose of a MLV BVDV vaccine has proven sufficient for providing protection from infection, and the duration of immunity can extend for years in vaccinated cattle. In addition, cross-protection has been reported using MLV vaccines (Martin, et al., In "Proceedings of the Conference of Research Workers in Animal Diseases", 75:183 (1994)). However, existing MLV vaccines do not allow for the differentiation between vaccinated and naturally-infected animals.

Thus, it is clear that a need exists for new vaccines for controlling the spread of BVDV. Such a vaccine(s) could be invaluable in future national or regional BVDV eradication programs, and could also be combined with other cattle vaccines, representing a substantial advance in the industry. A more effective vaccine for controlling and monitoring the spread of BVDV would be a "marked" vaccine. Such a vaccine could either contain an additional antigenic determinant which is not present in wild-type virus, or lack an antigenic determinant which is present in wild-type virus. With respect to the former, vaccinated animals mount an immune response to the "marker" immunogenic determinant, while non-vaccinated animals do not. Through the use of an immunological assay directed against the marker determinant, vaccinated animals could be differentiated from non-vaccinated, naturally-infected animals by the presence of antibodies to the marker determinant. In the case of the latter strategy, animals infected with the wild-type virus mount an immune response to the marker determinant, while non-infected, vaccinated animals do not, as a result of the determinant not being present in the marked vaccine. Through the use of an immunological assay directed against the marker determinant, infected animals could be differentiated from vaccinated, non-infected animals. In both scenarios, by culling out the infected animals, the herd could, over time, become BVDV-free. In addition to the benefit of removing the threat of BVDV disease, certification of a herd as BVDV-free has direct freedom of trade economic benefits.

SUMMARY

In one embodiment, the present invention provides a chimeric pestivirus, wherein said chimeric pestivirus comprises a bovine viral diarrhea virus which does not express its homologous $E^{rns}$ protein, further wherein said chimeric pestivirus expresses a heterologous $E^{rns}$ protein derived from another pestivirus, or a natural, synthetic or genetic variant of said heterologous $E^{rns}$ protein.

In another embodiment, the present invention provides the chimeric pestivirus as described above, wherein the heterologous $E^{rns}$ protein of said chimeric pestivirus, or the natural, synthetic or genetic variant of said heterologous $E^{rns}$ protein, is derived from a pestivirus selected from the group consisting of a reindeer pestivirus, a giraffe pestivirus, and a pronghorn antelope pestivirus.

In a different embodiment, the present invention provides the chimeric pestivirus as described above, wherein the heterologous $E^{rns}$ protein of said chimeric pestivirus has at least one $E^{rns}$ epitope which is not present in wild-type bovine viral diarrhea virus.

In a separate embodiment, the present invention provides the chimeric pestivirus as described above, wherein the heterologous $E^{rns}$ protein of said chimeric pestivirus lacks at least one $E^{rns}$ epitope which is present in wild-type bovine viral diarrhea virus.

In one embodiment, the present invention provides a culture of the chimeric pestivirus as described above.

In another embodiment, the present invention provides a cell line or host cell comprising the chimeric pestivirus as described above.

In yet another embodiment, the present invention provides a polynucleotide molecule encoding for the chimeric pestivirus as described above.

In a different embodiment, the present invention provides an immunogenic composition comprising the chimeric pestivirus as described above and a veterinarily-acceptable carrier.

In a separate embodiment, the present invention provides the immunogenic composition as described above, wherein the veterinarily-acceptable carrier is an adjuvant.

In yet another embodiment, the present invention provides the immunogenic composition as described above, wherein said chimeric pestivirus is live attenuated.

In still another embodiment, the present invention provides the immunogenic composition as described above, wherein said chimeric pestivirus is inactivated.

In a different embodiment, the present invention provides the immunogenic composition as described above, further comprising one or more additional antigens useful for treating or preventing the spread of one or more additional pathogenic microorganisms in an animal.

In a separate embodiment, the present invention provides an immunogenic composition comprising the polynucleotide molecule encoding for the chimeric pestivirus as described above and a veterinarily-acceptable carrier.

In one embodiment, the present invention provides a vaccine comprising the chimeric pestivirus as described above and a veterinarily-acceptable carrier.

In another embodiment, the present invention provides the vaccine as described above, wherein the veterinarily-acceptable carrier is an adjuvant.

In a different embodiment, the present invention provides the vaccine as described above, wherein said chimeric pestivirus is live attenuated.

In yet another embodiment, the present invention provides the vaccine as described above, wherein said chimeric pestivirus is inactivated.

In still another embodiment, the present invention provides the vaccine as described above, further comprising one or more additional antigens useful for treating or preventing the spread of one or more additional pathogenic microorganisms in an animal.

In a separate embodiment, the present invention provides a vaccine comprising a polynucleotide molecule encoding for the chimeric pestivirus as described above and a veterinary acceptable carrier.

In one embodiment, the present invention provides a kit comprising, in at least one container, a vaccine comprising the chimeric pestivirus as described above.

In another embodiment, the present invention provides a method of treating or preventing the spread of bovine viral diarrhea virus infection, wherein a vaccine comprising the chimeric pestivirus as described above is administered to an animal.

In a different embodiment, the present invention provides method of vaccinating an animal, wherein a DIVA pestivirus vaccine is administered to said animal, and wherein said DIVA pestivirus vaccine comprises the chimeric pestivirus as described above, further wherein said chimeric pestivirus has at least one $E^{rns}$ epitope which is not present in wild-type bovine viral diarrhea virus.

In a separate embodiment, the present invention provides method of vaccinating an animal, wherein a DIVA pestivirus vaccine is administered to said animal, and wherein said DIVA vaccine comprises the chimeric pestivirus as described above, further wherein said chimeric pestivirus lacks at least one $E^{rns}$ epitope which is present in wild-type bovine viral diarrhea virus.

In yet another embodiment, the present invention provides method of differentiating between an animal vaccinated with a vaccine comprising the chimeric pestivirus as described above and an animal infected with wild type bovine viral diarrhea virus, wherein the animal vaccinated with said vaccine generates antibodies to at least one $E^{rns}$ epitope which is present in the chimeric pestivirus of said vaccine, but which is not present in wild-type bovine viral diarrhea virus, said method comprising the steps of:

a) obtaining a serum sample from the animals;
b) assaying said samples for the presence or absence of the antibodies;
c) identifying the animal having said antibodies as having been vaccinated with said vaccine; and
d) identifying the animal lacking said antibodies as having been infected with the wild type BVDV.

In still another embodiment, the present invention provides method of differentiating between an animal infected with wild-type bovine viral diarrhea virus and an animal vaccinated with a vaccine comprising the chimeric pestivirus as described above, wherein the animal infected with wild type bovine viral diarrhea virus generates antibodies to at least one $E^{rns}$ epitope which is present in wild-type bovine viral diarrhea virus, but which is not present in the chimeric pestivirus of said vaccine, said method comprising the steps of:

a) obtaining a serum sample from the animals;
b) assaying said samples for the presence or absence of the antibodies;
c) identifying the animal having said antibodies as having been infected with the wild type BVDV; and
d) identifying the animal lacking said antibodies as having been vaccinated with said vaccine.

In one embodiment, the present invention provides diagnostic kit for differentiating between an animal vaccinated with a vaccine comprising the chimeric pestivirus as described above and an animal infected with wild type bovine viral diarrhea virus, said kit comprising reagents capable of detecting antibodies to at least one $E^{rns}$ epitope which is present in the chimeric pestivirus of the vaccine, but which is not present in wild-type bovine viral diarrhea virus.

In another embodiment, the present invention provides diagnostic kit for differentiating between an animal infected with wild type bovine viral diarrhea virus and an animal vaccinated with a vaccine comprising the chimeric pestivirus as described above, said kit comprising reagents capable of detecting antibodies to at least one $E^{rns}$ epitope which is present in wild-type bovine viral diarrhea virus, but which is not present in the chimeric pestivirus of the vaccine.

In yet another embodiment, the present invention provides an antibody which recognizes an epitope of $E^{rns}$ which is present in the chimeric pestivirus as described above, but which epitope is not present in wild-type bovine viral diarrhea virus.

In a different embodiment, the present invention provides an antibody which recognizes an epitope present in wild-type bovine viral diarrhea virus, but which epitope is not present in the chimeric pestivirus as described above.

In another embodiment, a chimeric pestivirus as described herein is used in the preparation of a medicament for the prevention or treatment of infections caused by BVDV.

DETAILED DESCRIPTION

The following definitions may be applied to terms employed in the description of embodiments of the invention. The following definitions supercede any contradictory definitions contained in each individual reference incorporated herein by reference.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular.

The term "amino acid," as used herein, refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, carboxyglutamate, and O-phosphoserine. Stereoisomers (e.g., D-amino acids) of the twenty conventional amino acids, unnatural amino acids such as $\alpha$ and $\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\sigma$-N-methylarginine, and other similar amino acids and imino acids.

Amino acid analogs refer to compounds that have the same basic chemical structure as a naturally occurring amino acid, i.e., a carbon that is bound to a hydrogen, a carboxyl group, an amino group, and an R group. Exemplary amino acid analogs include, for example, homoserine, norleucine, methionine sulfoxide, and methionine methyl sulfonium. Such analogs have modified R groups (e.g., norleucine) or modified peptide backbones, but retain the same essential chemical structure as a naturally occurring amino acid. Amino acid mimetics refer to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission.

The term "animal" as used herein, is meant to include any animal that is susceptible to BVDV infections, including but not limited to bovine, ovine, caprine and porcine species, both domesticated and wild.

The term "antibody" or "antibodies", as used herein, refers to an immunoglobulin molecule able to bind to an antigen by means of recognition of an epitope. Antibodies can be a polyclonal mixture or monoclonal. Antibodies can be intact immunoglobulins derived from natural sources or from recombinant sources, or can be immunoreactive portions of intact immunoglobulins. Antibodies can exist in a variety of forms including, for example, as, Fv, Fab', $F(ab')_2$, as well as in single chains.

The term "antigen" as used herein refers to a molecule that contains one or more epitopes (linear, conformational or both) that upon exposure to a subject will induce an immune response that is specific for that antigen. The term "antigen" can refer to attenuated, inactivated or modified live bacteria, viruses, fungi, parasites or other microbes. The term "antigen" as used herein can also refer to a subunit antigen, which is separate and discrete from a whole organism with which the antigen is associated in nature. The term "antigen" can also refer to antibodies, such as anti-idiotype antibodies or fragments thereof, and to synthetic peptide mimotopes that can mimic an antigen or antigenic determinant (epitope). The term "antigen" can also refer to an oligonucleotide or polynucleotide that expresses an antigen or antigenic determinant in vivo, such as in DNA immunization applications.

The terms "BVDV", "BVDV isolates" or "BVDV strains" as used herein refer to bovine viral diarrhea viruses, including but not limited to type I and type II, that consist of the viral genome, associated proteins, and other chemical constituents (such as lipids). A number of type I and type II bovine viral diarrhea viruses are known to those skilled in the art and are available through, e.g., the American Type Culture Collection (ATCC®). The bovine viral diarrhea virus has a genome in the form of RNA. RNA can be reverse transcribed into DNA for use in cloning. Thus, references made herein to nucleic acid and bovine viral diarrhea virus sequences encompass both viral RNA sequences and DNA sequences derived from the viral RNA sequences.

The term "cell line" or "host cell", as used herein means a prokaryotic or eukaryotic cell in which a virus can replicate and/or be maintained.

The term "chimeric" or "chimera" as used herein means a microorganism, for example a virus, containing genetic or physical components derived from more than one progenitor.

The term "culture" as used herein means a population of cells or microorganisms growing in the absence of other species or types.

The term "DIVA" as used herein means a vaccine which is able to differentiate infected from vaccinated animals.

An "epitope" is the specific site of the antigen which binds to a T-cell receptor or specific antibody, and typically comprises from about 3 amino acid residues to about 20 amino acid residues.

The term "heterologous", as used herein, means derived from a different species or strain.

The term "homologous", as used herein, means derived from the same species or strain.

The term "immunogenic composition", as used herein, means a composition that generates an immune response (i.e., has immunogenic activity) when administered alone or with a pharmaceutically acceptable carrier, to an animal. The immune response can be a cellular immune response mediated primarily by cytotoxic T-cells, or a humoral immune response mediated primarily by helper T-cells, which in turn activates B-cells leading to antibody production.

The term "pathogen" or "pathogenic microorganism" as used herein means a microorganism—for example a virus, bacterium, fungus, protozoan, or helminth—which is capable of inducing or causing a disease, illness, or abnormal state in its host animal.

The term "pestivirus" as used herein means a RNA virus from the genus *Pestivirus*, of the family Flaviviridae. Pestiviruses include, but are not limited to, BVDV (type 1 and type 2), Classical Swine Fever Virus (CSFV), and Border Disease Virus (BDV), as well as pestiviruses isolated from species such as wild boar, buffalo, eland, bison, alpaca, pudu, bongo, various deer species, giraffe, reindeer, chamois and pronghorn antelope (Vilcek and Nettleton; *Vet Microbiol.* 116:1-12 (2006))

The term "polynucleotide molecule" as used herein means an organic polymer molecule composed of nucleotide monomers covalently bonded in a chain. DNA (deoxyribonucleic acid) and RNA (ribonucleic acid) are examples of polynucleotides with distinct biological function.

The terms "prevent", "preventing" or "prevention", and the like, as used herein, mean to inhibit the replication of a microorganism, to inhibit transmission of a microorganism, or to inhibit a microorganism from establishing itself in its host. These terms and the like as used herein can also mean to inhibit or block one or more signs or symptoms of infection.

The term "therapeutically effective amount" as used herein means an amount of a microorganism, or a subunit antigen, or polypeptides, or polynucleotide molecules, and combinations thereof, sufficient to elicit an immune response in the subject to which it is administered. The immune response can comprise, without limitation, induction of cellular and/or humoral immunity.

The terms "treat", "treating" or "treatment", and the like, as used herein mean to reduce or eliminate an infection by a microorganism. These terms and the like as used herein can also mean to reduce the replication of a microorganism, to reduce the transmission of a microorganism, or to reduce the ability of a microorganism to establish itself in its host. These terms and the like as used herein can also mean to reduce, ameliorate, or eliminate one or more signs or symptoms of infection by a microorganism, or accelerate the recovery from infection by a microorganism.

The terms "vaccine" and "vaccine composition," as used herein, mean a composition which prevents or reduces an infection, or which prevents or reduces one or more signs or symptoms of infection. The protective effects of a vaccine composition against a pathogen are normally achieved by inducing in the subject an immune response, either a cell-mediated or a humoral immune response or a combination of both. Generally speaking, abolished or reduced incidences of infection, amelioration of the signs or symptoms, or accelerated elimination of the microorganism from the infected subjects are indicative of the protective effects of a vaccine composition. The vaccine compositions of the present invention provide protective effects against infections caused by BVDV.

The term "variant," as used herein, refers to a derivation of a given protein and/or gene sequence, wherein the derived sequence is essentially the same as the given sequence, but for mutational differences. Said differences may be naturally-occurring, or synthetically- or genetically-generated.

The term "veterinarily-acceptable carrier" as used herein refers to substances, which are within the scope of sound medical judgment, suitable for use in contact with the tissues of animals without undue toxicity, irritation, allergic response, and the like, commensurate with a reasonable benefit-to-risk ratio, and effective for their intended use.

The following description is provided to aid those skilled in the art in practicing the present invention. Even so, this description should not be construed to unduly limit the present invention as modifications and variations in the embodiments discussed herein can be made by those of ordinary skill in the art without departing from the spirit or scope of the present inventive discovery.

Viruses, Immunogenic Compositions, and Vaccines

The present invention provides immunogenic compositions and vaccines comprising one or more chimeric pestiviruses, wherein said chimeric pestiviruses comprise a bovine viral diarrhea virus which does not express its homologous $E^{rns}$ protein, but wherein said chimeric pestivirus expresses a heterologous $E^{rns}$ protein derived from another pestivirus, or a natural, synthetic or genetic variant of said heterologous $E^{rns}$ protein. The chimeric pestivirus can be selected from, but is not limited to, the group consisting of BVDV/reindeer pestivirus, BVDV/giraffe pestivirus, and BVDV/pronghorn antelope pestivirus chimeras.

In one embodiment, the BVDV/giraffe chimeric pestivirus is the strain deposited as UC 25547 with American Type Culture Collection (ATCC®), 10801 University Boulevard, Manassas, Va. 20110-2209, USA, and given the ATCC® deposit designation of PTA-9938. In one embodiment, the BVDV/pronghorn antelope chimeric pestivirus is the strain deposited as UC 25548 with ATCC® and given the ATCC® deposit designation of PTA-9939. In one embodiment, the BVDV/reindeer chimeric pestivirus is the strain deposited as UC 25549 with ATCC® and given the ATCC® deposit designation of PTA-9940.

Chimeric pestiviruses of the present invention can be propagated in cells, cell lines and host cells. Said cells, cell lines or host cells may be for example, but not limited to, mammalian cells and non-mammalian cells, including insect and plant cells. Cells, cell lines and host cells in which chimeric pestiviruses of the present invention may be propagated are readily known and accessible to those of ordinary skill in the art.

The chimeric pestiviruses of the present invention can be attenuated or inactivated prior to use in an immunogenic composition or vaccine. Methods of attenuation and inactivation are well known to those skilled in the art. Methods for attenuation include, but are not limited to, serial passage in cell culture on a suitable cell line, ultraviolet irradiation, and chemical mutagenesis. Methods for inactivation include, but are not limited to, treatment with formalin, betapropriolactone (BPL) or binary ethyleneimine (BEI), or other methods known to those skilled in the art.

Inactivation by formalin can be performed by mixing the virus suspension with 37% formaldehyde to a final formaldehyde concentration of 0.05%. The virus-formaldehyde mixture is mixed by constant stirring for approximately 24 hours at room temperature. The inactivated virus mixture is then tested for residual live virus by assaying for growth on a suitable cell line.

Inactivation by BEI can be performed by mixing the virus suspension of the present invention with 0.1 M BEI (2-bromo-ethylamine in 0.175 N NaOH) to a final BEI concentration of 1 mM. The virus-BEI mixture is mixed by constant stirring for approximately 48 hours at room temperature, followed by the addition of 1.0 M sodium thiosulfate to a final concentration of 0.1 mM. Mixing is continued for an additional two hours. The inactivated virus mixture is tested for residual live virus by assaying for growth on a suitable cell line.

Immunogenic compositions and vaccines of the present invention can include one or more veterinarily-acceptable carriers. As used herein, a "veterinarily-acceptable carrier" includes any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others known to those skilled in the art. Stabilizers include albumin, among others known to the skilled artisan. Preservatives include merthiolate, among others known to the skilled artisan.

Adjuvants include, but are not limited to, the RIBI adjuvant system (Ribi Inc.), alum, aluminum hydroxide gel, oil-in water emulsions, water-in-oil emulsions such as, e.g., Freund's complete and incomplete adjuvants, Block co polymer (CytRx, Atlanta Ga.), SAF-M (Chiron, Emeryville Calif.), AMPHIGEN® adjuvant, saponin, Quil A, QS-21 (Cambridge Biotech Inc., Cambridge Mass.), GPI-0100 (Galenica Pharmaceuticals, Inc., Birmingham, Ala.) or other saponin fractions, monophosphoryl lipid A, Avridine lipid-amine adjuvant, heat-labile enterotoxin from *E. coli* (recombinant or otherwise), cholera toxin, or muramyl dipeptide, among many others known to those skilled in the art. The amounts and concentrations of adjuvants and additives useful in the context of the present invention can readily be determined by the skilled artisan. In one embodiment, the present invention contemplates immunogenic compositions and vaccines comprising from about 50 μg to about 2000 μg of adjuvant. In another embodiment adjuvant is included in an amount from about 100 μg to about 1500 μg, or from about 250 μg to about 1000 μg, or from about 350 μg to about 750 μg. In another embodiment, adjuvant is included in an amount of about 500 μg/2 ml dose of the immunogenic composition or vaccine.

The immunogenic compositions and vaccines can also include antibiotics. Such antibiotics include, but are not limited to, those from the classes of aminoglycosides, carbapenems, cephalosporins, glycopeptides, macrolides, penicillins, polypeptides, quinolones, sulfonamides, and tetracyclines. In one embodiment, the present invention contemplates immunogenic compositions and vaccines comprising from about 1 μg/ml to about 60 μg/ml of antibiotic. In another embodiment, the immunogenic compositions and vaccines comprise from about 5 μg/ml to about 55 μg/ml of antibiotic, or from about 10 μg/ml to about 50 μg/ml of antibiotic, or from about 15 μg/ml to about 45 μg/ml of antibiotic, or from about 20 μg/ml to about 40 μg/ml of antibiotic, or from about 25 μg/ml to about 35 μg/ml of antibiotic. In yet another embodiment, the immunogenic compositions and vaccines comprise less than about 30 μg/ml of antibiotic.

Immunogenic compositions and vaccines of the invention can further include one or more other immunomodulatory agents such as, e.g., interleukins, interferons, or other cytokines, suitable amounts of which can be determined by the skilled artisan.

Immunogenic compositions and vaccines of the present invention can include one or more polynucleotide molecules encoding for a chimeric pestivirus. Either DNA or RNA molecules encoding all of the chimeric pestivirus genome, or one or more open reading frames, can be used in immunogenic compositions or vaccines. The DNA or RNA molecule can be administered absent other agents, or it can be administered together with an agent facilitating cellular uptake (e.g., liposomes or cationic lipids). Total polynucleotide in the immunogenic composition or vaccine will generally be between about 0.1 μg/ml and about 5.0 mg/ml. In another embodiment, the total polynucleotide in the immunogenic composition or vaccine will be from about 1 μg/ml and about 4.0 mg/ml, or from about 10 μg/ml and about 3.0 mg/ml, or from about 100 μg/ml and about 2.0 mg/ml, Vaccines and vaccination procedures that utilize nucleic acids (DNA or mRNA) have been well described in the art, for example, U.S. Pat. No. 5,703,055, U.S. Pat. No. 5,580,859, U.S. Pat. No. 5,589,466, all of which are incorporated herein by reference.

Immunogenic compositions and vaccines of the present invention can also include additional BVDV antigens, for example, those described in U.S. Pat. No. 6,060,457, U.S. Pat. No. 6,015,795, U.S. Pat. No. 6,001,613, and U.S. Pat. No. 5,593,873, all of which are herein incorporated by reference.

In addition to one or more chimeric pestiviruses, immunogenic compositions and vaccines can include other antigens. Antigens can be in the form of an inactivated whole or partial preparation of the microorganism, or in the form of antigenic molecules obtained by genetic engineering techniques or chemical synthesis. Other antigens appropriate for use in accordance with the present invention include, but are not limited to, those derived from pathogenic bacteria such as *Haemophilus somnus, Haemophilus parasuis, Bordetella bronchiseptica, Bacillus anthracis, Actinobacillus pleuropneumonie, Pasteurella multocida, Mannhemia haemolytica, Mycoplasma bovis, Mycobacterium bovis, Mycobacterium paratuberculosis, Clostridial* spp., *Streptococcus uberis, Staphylococcus aureus, Erysipelothrix rhusopathiae, Chlamydia* spp., *Brucella* spp., *Vibrio* spp., *Salmonella enterica* serovars and *Leptospira* spp. Antigens can also be derived from pathogenic fungi such as *Candida*, protozoa such as *Cryptosporidium parvum, Neospora canium, Toxoplasma gondii, Eimeria* spp., *Babesia* spp., *Giardia* spp., or helminths such as *Ostertagia, Cooperia, Haemonchus*, and *Fasciola*. Additional antigens include pathogenic viruses such as bovine coronavirus, bovine herpesviruses-1,3,6, bovine parainfluenza virus, bovine respiratory syncytial virus, bovine leukosis virus, rinderpest virus, foot and mouth disease virus, rabies virus, and influenza virus.

Forms, Dosages, Routes of Administration

Immunogenic compositions and vaccines of the present invention can be administered to animals to induce an effective immune response against BVDV. Accordingly, the present invention provides methods of stimulating an effective immune response against BVDV, by administering to an animal a therapeutically effective amount of an immunogenic composition or vaccine of the present invention described herein.

Immunogenic compositions and vaccines of the present invention can be made in various forms depending upon the route of administration. For example, the immunogenic compositions and vaccines can be made in the form of sterile aqueous solutions or dispersions suitable for injectable use, or made in lyophilized forms using freeze-drying techniques. Lyophilized immunogenic compositions and vaccines are typically maintained at about 4° C., and can be reconstituted in a stabilizing solution, e.g., saline or and HEPES, with or without adjuvant. Immunogenic compositions and vaccines can also be made in the form of suspensions or emulsions.

Immunogenic compositions and vaccines of the present invention include a therapeutically effective amount of one or more of the above-described chimeric pestiviruses. Purified viruses can be used directly in an immunogenic composition or vaccine, or can be further attenuated, or inactivated. Typically, an immunogenic composition or vaccine contains between about $1\times10^2$ and about $1\times10^{12}$ virus particles, or between about $1\times10^3$ and about $1\times10^{11}$ virus particles, or between about $1\times10^4$ and about $1\times10^{10}$ virus particles, or between about $1\times10^5$ and about $1\times10^9$ virus particles, or between about $1\times10^6$ and about $1\times10^8$ virus particles. The precise amount of a virus in an immunogenic composition or vaccine effective to provide a protective effect can be determined by a skilled artisan.

The immunogenic compositions and vaccines generally comprise a veterinarily-acceptable carrier in a volume of between about 0.5 ml and about 5 ml. In another embodiment the volume of the carrier is between about 1 ml and about 4 ml, or between about 2 ml and about 3 ml. In another embodiment, the volume of the carrier is about 1 ml, or is about 2 ml, or is about 5 ml. Veterinarily-acceptable carriers suitable for use in immunogenic compositions and vaccines can be any of those described hereinabove.

Those skilled in the art can readily determine whether a virus needs to be attenuated or inactivated before administration. In another embodiment of the present invention, a chimeric pestivirus can be administered directly to an animal without additional attenuation. The amount of a virus that is therapeutically effective can vary depending on the particular virus used, the condition of the animal and/or the degree of infection, and can be determined by a skilled artisan.

In accordance with the methods of the present invention, a single dose can be administered to animals, or, alternatively, two or more inoculations can take place with intervals of from about two to about ten weeks. Boosting regimens can be required and the dosage regimen can be adjusted to provide optimal immunization. Those skilled in the art can readily determine the optimal administration regimen.

Immunogenic compositions and vaccines can be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which can contain excipients such as salts, carbohydrates and buffering agents (preferably to a pH of from about 3 to about 9, or from about 4 to about 8, or from about 5 to about 7.5, or from about 6 to about 7.5, or about 7 to about 7.5), but, for some applications, they can be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, can readily be accomplished using standard pharmaceutical techniques well known to those skilled in the art.

The solubility of compounds used in the preparation of parenteral solutions can be increased by the use of appropriate formulation techniques known to the skilled artisan, such as the incorporation of solubility-enhancing agents including buffers, salts, surfactants, liposomes, cyclodextrins, and the like.

Formulations for parenteral administration can be formulated to be immediate and/or modified release. Modified release formulations include delayed, sustained, pulsed, controlled, targeted and programmed release. Thus compounds of the invention can be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

Immunogenic compositions and vaccines of the present invention can also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes can also be used. Typical carriers include alcohol, water, mineral oil, liquid petrolatum, white petrolatum, glycerin, polyethylene glycol and propylene glycol. Penetration enhancers can be incorporated. See, for example, Finnin and Morgan, *J. Pharm Sci,* 88 (10):955-958 (1999).

Other means of topical administration include delivery by electroporation, iontophoresis, phonophoresis, sonophoresis and microneedle or needle-free (e.g. Powderject™, Bioject™, etc.) injection.

Formulations for topical administration can be formulated to be immediate and/or modified release. Modified release formulations include delayed, sustained, pulsed, controlled, targeted and programmed release.

Immunogenic compositions and vaccines can also be administered intranasally or by inhalation, typically in the form of a dry powder (either alone or as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder can comprise a bioadhesive agent, for example, chitosan or cyclodextrin.

The pressurized container, pump, spray, atomizer, or nebulizer contains a solution or suspension of the compound (s) of the invention comprising, for example, ethanol, aqueous ethanol, or a suitable alternative agent for dispersing, solubilizing, or extending release of the active, a propellant (s) as solvent and an optional surfactant, such as sorbitan trioleate, oleic acid, or an oligolactic acid.

Prior to use in a dry powder or suspension formulation, the drug product is generally micronized to a size suitable for delivery by inhalation (typically less than about 5 microns). This can be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropylmethylcellulose), blisters and cartridges for use in an inhaler or insufflator can be formulated to contain a powder mix of the compound of the invention, a suitable powder base such as lactose or starch and a performance modifier such as l-leucine, mannitol, or magnesium stearate. The lactose can be anhydrous or in the form of the monohydrate. Other suitable excipients include dextran, glucose, maltose, sorbitol, xylitol, fructose, sucrose and trehalose.

A suitable solution formulation for use in an atomizer using electrohydrodynamics to produce a fine mist can contain from about 1 μg to about 20 mg of the compound of the invention per actuation and the actuation volume can vary from about 1 μl to about 100 μl. In another embodiment, the amount of compound per actuation can range from about 100 μg to about 15 mg, or from about 500 μg to about 10 mg, or from about 1 mg to about 10 mg, or from about 2.5 μg to about 5 mg. In another embodiment, the actuation volume can range from about 5 μl to about 75 μl, or from about 10 μl to about 50 μl, or from about 15 μl to about 25 μl. A typical formulation can comprise the compound of the invention, propylene glycol, sterile water, ethanol and sodium chloride. Alternative solvents which can be used instead of propylene glycol include glycerol and polyethylene glycol.

Formulations for inhaled/intranasal administration can be formulated to be immediate and/or modified release using, for example, PGLA. Modified release formulations include delayed, sustained, pulsed, controlled, targeted and programmed release.

In the case of dry powder inhalers and aerosols, the dosage unit is generally determined by means of a valve which delivers a metered amount. Units in accordance with the invention are typically arranged to administer a metered dose or "puff" containing from about 10 ng to about 100 μg of the compound of the invention. In another embodiment, the amount of compound administered in a metered dose is from about 50 ng to about 75 μg, or from about 100 ng to about 50 μg, or from about 500 ng to about 25 μg, or from about 750 ng to about 10 μg, or from about 1 μg to about 5 μg. The overall daily dose will typically be in the range from about 1 μg to about 100 mg which can be administered in a single dose or, more usually, as divided doses throughout the day. In another embodiment, the overall daily dose can range from about 50 μg to about 75 mg, or from about 100 μg to about 50 mg, or from about 500 μg to about 25 mg, or from about 750 μg to about 10 mg, or from about 1 mg to about 5 mg.

Immunogenic compositions and vaccines of the present invention can also be administered orally or perorally, that is into a subject's body through or by way of the mouth and involves swallowing or transport through the oral mucosa (e.g., sublingual or buccal absorption) or both. Suitable flavors, such as menthol and levomenthol, or sweeteners, such as saccharin or saccharin sodium, can be added to those formulations of the invention intended for oral or peroral administration.

Immunogenic compositions and vaccines of the present invention can be administered rectally or vaginally, for example, in the form of a suppository, pessary, or enema. Cocoa butter is a traditional suppository base, but various alternatives can be used as appropriate. Formulations for rectal/vaginal administration can be formulated to be immediate and/or modified release. Modified release formulations include delayed, sustained, pulsed, controlled, targeted and programmed release.

Immunogenic compositions and vaccines of the present invention can also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, can be incorporated together with a preservative, such as benzalkonium chloride. Such formulations can also be delivered by iontophoresis.

Formulations for ocular/aural administration can be formulated to be immediate and/or modified release. Modified release formulations include delayed, sustained, pulsed, controlled, targeted and programmed release.

The immunogenic compositions and vaccines of the present invention can be used in the preparation of a medicament for treating or preventing the spread of bovine viral diarrhea virus infection in an animal.

The immunogenic compositions and vaccines of the present invention can be used in the preparation of a medicament for administering to an animal, wherein the medicament is a DIVA pestivirus vaccine comprising a chimeric pestivirus comprising a bovine viral diarrhea virus which does not express its homologous $E^{ms}$ protein, and wherein said chimeric pestivirus expresses a heterologous $E^{ms}$ protein derived from another pestivirus, or a natural, synthetic or genetic variant of said heterologous $E^{ms}$ protein. In one embodiment, the chimeric pestivirus has at least one $E^{ms}$ epitope which is not present in wild-type bovine viral diarrhea virus. In another embodiment the chimeric pestivirus lacks at least one $E^{ms}$ epitope which is present in wild-type bovine viral diarrhea virus.

Detection, Diagnostic Methods

The present invention provides methods of determining the origin of a pestivirus present in an animal subject.

Vaccination which utilizes a DIVA vaccine—one which is able to differentiate infected from vaccinated animals—provides a means for determining the origin of a pestivirus present in an animal subject. This differentiation can be accomplished via any of various diagnostic methods, including but not limited to ELISA, Western blotting and PCR. These and other methods are readily recognized and known to one of ordinary skill in the art.

The chimeric pestiviruses of the present invention can be distinguished from wild-type BVDV strains in both their genomic composition and proteins expressed. Such distinction allows for discrimination between vaccinated and infected animals. For example, a determination can be made as to whether an animal testing positive for BVDV in certain laboratory tests carries a wild-type BVDV strain, or carries a chimeric pestivirus of the present invention previously obtained through vaccination.

A variety of assays can be employed for making the determination. For example, virus can be isolated from the animal testing positive for BVDV, and nucleic acid-based assays can be used to determine the presence of a chimeric pestivirus genome, indicative of prior vaccination. The nucleic acid-based assays include Southern or Northern blot analysis, PCR, and sequencing. Alternatively, protein-based assays can be employed. In protein-based assays, cells or tissues suspected of an infection can be isolated from the animal testing positive for BVDV. Cellular extracts can be made from such cells or tissues and can be subjected to, e.g., Western Blot, using appropriate antibodies against viral proteins that can distinctively identify the presence of either the chimeric pestivirus previously inoculated, or wild-type BVDV.

The extent and nature of the immune responses induced in the animal can be assessed by using a variety of techniques. For example, sera can be collected from the inoculated animals and tested for the presence or absence of antibodies specific for the chimeric virus, e.g., in a conventional virus neutralization assay. Detection of responding cytotoxic T-lymphocytes (CTLs) in lymphoid tissues can be achieved by assays such as T cell proliferation, as indicative of the induction of a cellular immune response. The relevant techniques are well described in the art, e.g., Coligan et al. *Current Protocols in Immunology*, John Wiley & Sons Inc. (1994).

Kits

Inasmuch as it may be desirable to administer an immunogenic composition or vaccine in combination with additional compounds, for example, for the purpose of treating a particular disease or condition, it is within the scope of the present invention that an immunogenic composition or vaccine can conveniently be included in, or combined in, the form of a kit suitable for administration or co-administration of the compositions.

Thus, kits of the present invention can comprise one or more separate pharmaceutical compositions, at least one of which is an immunogenic composition or vaccine in accordance with the present invention, and a means for separately retaining said compositions, such as a container, divided bottle, or divided foil packet. An example of such a kit is a syringe and needle, and the like. A kit of the present invention is particularly suitable for administering different dosage forms, for example, oral or parenteral, for administering the separate compositions at different dosage intervals, or for titrating the separate compositions against one another. To assist one administering a composition of the present invention, the kit typically comprises directions for administration.

Another kit of the present invention can comprise one or more reagents useful for the detection of and differentiation between a BVDV-infected animal and a chimeric pestivirus-vaccinated animal. The kit can include reagents for analyzing a sample for the presence of whole BVDV, or BVDV polypeptides, epitopes or polynucleotide sequences which are not present in the chimeric pestivirus of the immunogenic composition or vaccine. Alternatively, kits of the present invention can include reagents for analyzing a sample for the presence of a chimeric pestivirus, or polypeptides, epitopes or polynucleotide sequences which are not present in wild-type BVDV. The presence of virus, polypeptides, or polynucleotide sequences can be determined using antibodies, PCR, hybridization, and other detection methods known to those of skill in the art.

Another kit of the present invention can provide reagents for the detection of antibodies against particular epitopes. The epitopes are either present in the chimeric pestivirus of the present invention and not present in wild type BVDV, or alternatively, are present in wild-type BVDV and not present in the chimeric pestivirus of the present invention. Such reagents are useful for analyzing a sample for the presence of antibodies, and are readily known and available to one of ordinary skill in the art. The presence of antibodies can be determined using standard detection methods known to those of skill in the art.

In certain embodiments, the kits can include a set of printed instructions or a label indicating that the kit is useful for the detection and differentiation of BVDV-infected animals from chimeric pestivirus-vaccinated animals.

Antibody, Antibodies

Antibodies can either be monoclonal, polyclonal, or recombinant. Conveniently, the antibodies can be prepared against the immunogen or a portion thereof. For example, a synthetic peptide based on the amino acid sequence of the immunogen, or prepared recombinantly by cloning techniques or the natural gene product and/or portions thereof can be isolated and used as the immunogen. Immunogens can be used to produce antibodies by standard antibody production technology well known to those skilled in the art, such as described generally in Harlow and Lane, "Antibodies: A Laboratory Manual", Cold Spring Harbor Laboratory, Cold Spring Harbor, N.Y., (1988) and Borrebaeck, "Antibody Engineering—A Practical Guide", W.H. Freeman and Co. (1992). Antibody fragments can also be prepared from the antibodies, and include Fab, $F(ab')_2$, and Fv, by methods known to those skilled in the art.

In the production of antibodies, screening for the desired antibody can be accomplished by standard methods in immunology known in the art. Techniques not specifically described are generally followed as in Stites, et al. (eds), "Basic and Clinical Immunology" (8th Edition), Appleton and Lange, Norwalk, Conn. (1994) and Misheli and Shiigi (eds), "Selected Methods in Cellular Immunology", W.H. Freeman and Co., New York (1980). In general, ELISAs and Western blotting are the preferred types of immunoassays. Both assays are well known to those skilled in the art. Both polyclonal and monoclonal antibodies can be used in the assays. The antibody can be bound to a solid support substrate or conjugated with a detectable moiety or be both bound and conjugated as is well known in the art. (For a general discussion of conjugation of fluorescent or enzymatic moieties, see Johnstone and Thorpe, "Immunochemistry in Practice", Blackwell Scientific Publications, Oxford (1982).) The binding of antibodies to a solid support substrate is also well known in the art. (For a general discussion, see Harlow and Lane (1988) and Borrebaeck (1992).) The detectable moieties contemplated for use in the present invention can include, but are not limited to, fluorescent, metallic, enzymatic and radioactive markers such as biotin, gold, ferritin, alkaline phosphatase, b-galactosidase, peroxidase, urease, fluorescein, rhodamine, tritium, $^{14}C$ and iodination.

The present invention is further illustrated by, but by no means limited to, the following examples.

EXAMPLE 1

Construction and Serological Characterization of Chimeric Pestiviruses

*E. coli* K12 GM2163 [F-ara-14, leuB6, thi-1, fhuA31, lacY1, tsx-78, galK2, gatT22, supE44, hisG4, rpsL136, ($Str^r$), xyl-5, mtl-1, dam13::Tn9($Cam^r$), dcm-6, mcrB1, hsdR2($rk^-mk^-$), mcrA] harbors a plasmid containing the full length genomic cDNA of bovine viral diarrhea virus strain NADL (BVDV-NADL), obtained from Dr. R. Donis, University of Nebraska.

RD cells (bovine testicular cells transformed with SV40; obtained from Dr. R. Donis) were maintained in OptiMEM supplemented with 3% horse serum, 1% non-essential amino acids (NEAA) in modified Eagle's medium (MEM), 2 mM GlutaMax and 10 ug/ml Gentamicin. BK-6 cells were obtained from Pfizer Global Manufacturing (PGM). Cells were grown in Dulbecco's modified Eagles' medium (DMEM) supplemented with 5% horse serum or donor calf serum (PGM), 2 mM Glutamax, and 1% Antibiotic and Antimycotic. All medium components except where indicated were purchased from Invitrogen (Carlsbad, Calif.). All cells were maintained at 37° C. in a 5% $CO_2$ environment.

Monoclonal antibody (MAb) 15C5 specific to BVDV $E^{rns}$ was purchased from IDEXX (Westbrook, Me.). MAb 20.10.6 against BVDV NS3 was provided by Dr. E. Dubovi (Cornell University). MAbs WS 363, WS 373 and WS 371, having specificity for the Border Disease virus (BDV) $E^{rns}$ protein, were obtained from Veterinary Laboratories Agency (Surrey, UK). Bovine serum samples #77, #816, #1281, and #1434 were obtained internally at Pfizer.

Chimeric pestiviruses were generated by replacing the $E^{rns}$ gene of the BVDV-NADL strain with the $E^{rns}$ gene of giraffe (G-$E^{rns}$), reindeer (R-$E^{rns}$), or pronghorn antelope (P-$E^{rns}$) pestivirus using an overlapping PCR method. Either PfuUltra™ II fusion HS DNA polymerase (Stratagene; La Jolla, Calif.) or Platinum® Taq DNA Polymerase High Fidelity (Invitrogen) was used. The oligonucleotide primers (with accompanying SEQ ID NOs) for overlapping PCRs and for generating a full length viral DNA are listed in Table 1.

TABLE 1

Oligonucleotide primers used for PCR amplification

| SEQ ID NO | Name | Origin | Sequences (5'-3') | Primer Binding Site (underlined sequence) |
|---|---|---|---|---|
| 1 | Oligo B-5 | T7 + NADL | GTGTTAATACGACTCACTATAG<br>TATACGAGAATTAGAAAAGGC | T7 promoter |
| 2 | Oligo 84 | NADL | GGGGGCTGTTAGAGGTCTTCC | |
| 3 | Oligo 127 | G-$E^{rns}$ + NADL | AATTCCACTGGGTGATGTTCTCTC<br>CCATTGTAACTTGAAACAAAACT | G-$E^{rns}$ N-terminus |
| 4 | Oligo 128 | G-$E^{rns}$ | GAGAACATCACCCAGTGGAA | |
| 5 | Oligo 129 | G-$E^{rns}$ | TGCCTGGGCTCCAAACCATGT | |
| 6 | Oligo 130 | G-$E^{rns}$ + NADL | AACATGGTTTGGAGCCCACGCA<br>GCTTCCCCTTACTGTGATGTCG | G-$E^{rns}$ C-terminus |
| 7 | Oligo 131 | R-$E^{rns}$ + NADL | GGTTCCACTGTGTTATATTCTCTC<br>CCATTGTAACTTGAAACAAAACT | R-$E^{rns}$ N-terminus |
| 8 | Oligo 132 | R-$E^{rns}$ | GAGAATATAACACAGTGGAACC | |
| 9 | Oligo 133 | R-$E^{rns}$ | TGCATTAGCTCCGAACCACGTT | |
| 10 | Oligo 134 | R-$E^{rns}$ + NADL | AACGTGGTTCGGAGCTAATGCA<br>GCTTCCCCTTACTGTGATGTCG | R-$E^{rns}$ C-terminus |
| 11 | Oligo 135 | P-$E^{rns}$ + NADL | GGTTCCACTGAGTTATATTCAC<br>TCCCATTGTAACTTGAAACA | P-$E^{rns}$ N-terminus |
| 12 | Oligo 136 | P-$E^{rns}$ | GTGAATATAACTCAGTGGAACC | |
| 13 | Oligo 137 | P-$E^{rns}$ | TGCCTGTGCCCCAAACCATGT | |
| 14 | Oligo 138 | P-$E^{rns}$ + NADL | AACATGGTTTGGGGCACAGGCA<br>GCTTCCCCTTACTGTGATGTCG | P-$E^{rns}$ C-terminus |
| 15 | Oligo 175 | NADL | GTTATCAATAGTAGCCACAGAAT | |
| 16 | Oligo 177 | NADL | TCCACCCTCAATCGACGCTAAA | |
| 17 | Oligo 237 | CM5960 | CCCTGAGGCCTTCTGTTCTGAT | |
| 18 | Oligo P7 | CM5960 | CACTTGTCGGAGGTACTACTACT | |
| 19 | Oligo P8 | CM5960 | CTTGTCTATCTTATCTCTTATTGC | |
| 20 | Oligo P3 | CM5960 | ACTATCTGAACAGTTGGACAGG | |
| 21 | Oligo 296-1 | T7 + CM53637 | GTGTTAATACGACTCACTATA<br>GTATACGAGATTAGCTAAAG | T7 promoter |
| 22 | Oligo 297 | P-$E^{rns}$ + CM53637 | CCAGGTTCCACTGAGTTATATTCAC<br>TCCTGTTACCAGCTGAAGCAGAA | P-$E^{rns}$ N-terminus |

TABLE 1-continued

| Oligonucleotide primers used for PCR amplification | | | | |
|---|---|---|---|---|
| SEQ ID NO | Name | Origin | Sequences (5'-3') | Primer Binding Site (underlined sequence) |
| 23 | Oligo 298 | P-$E^{rns}$ + CM53637 | AACATGGTTTGGGGCACAGGCA GCAAGTCCATACTGTAAAGTG | P-$E^{rns}$ C-terminus |
| 24 | Oligo 299 | CM53637 | TTAATGCCCTCCCTGTCTCTACCACCT | |
| 25 | Oligo 300 | CM53637 | AGGATGAGGATCTAGCAGTGGATCT | |
| 26 | Oligo 303 | CM53637 | CCATAGCCATCTGCTCAGACAGTA | |
| 27 | Oligo 92-1 | CM53637 | GGGGCTGTCAGAGGCATCCTCTAGTC | |
| 28 | Oligo 321 | CM53637 | AGCCACTACACCTGTCACGAGAAG | |
| 29 | Oligo 250 | NADL | CACCATGAAAATAGTGCCCAAAGAATC | NADL-C C terminus |
| 30 | Oligo 252 | NADL | TTAAGCGTATGCTCCAAACCACGTC | NADL-$E^{rns}$ C terminus |

Plasmid containing the full length cDNA of BVDV-NADL was extracted from dam-*E. coli* K12 GM2163. The plasmid was methylated in vitro with dam methyltransferase and S-adenosylmethionine (New England Biolabs; Ipswich, Mass.). G-$E^{rns}$, R-$E^{rns}$, and P-$E^{rns}$ genes (GenBank accession numbers NC_003678, NC_003677, and AY781152, respectively) were synthesized and cloned into a cloning vector.

For construction of chimeric BVDV-NADL/G-$E^{rns}$ DNA, a fragment of BVDV-NADL encoding for the 5'UTR to the 3' end of C gene was amplified by PCR from methylated plasmid with primers Oligo B-5 and Oligo 127. The G-$E^{rns}$ gene was amplified by PCR from the plasmid DNA containing the G-$E^{rns}$ gene with Oligo 128 and Oligo 129. A BVDV fragment encoding for E1 to the 3'UTR was amplified by PCR from methylated plasmid with Oligo 130 and Oligo 84. The PCR products were gel purified using QIAquick Gel Extraction Kit (Qiagen; Valencia, Calif.). The purified PCR products were treated with Dpn I and Exonuclease 1 (New England Biolabs). The treated PCR products were assembled to create a full length chimeric BVDV-NADL/G-$E^{rns}$ genome by PCR using Oligo B-5 and Oligo 84.

For construction of chimeric BVDV-NADL/P-$E^{rns}$ DNA, a fragment of BVDV-NADL encoding for the 5'UTR to the 3' end of C gene was amplified by PCR from methylated plasmid with primers Oligo B-5 and Oligo 131, The R-$E^{rns}$ gene was amplified by PCR from the plasmid containing R-$E^{rns}$ gene with Oligo 132 and Oligo 133. A BVDV fragment encoding for E1 to the 3'UTR was amplified by PCR from methylated plasmid with Oligo 134 and Oligo 84. The PCR products were gel purified with QIAquick Gel Extraction Kit. The purified PCR products were treated with Dpn I and Exonuclease 1. The treated PCR products were assembled to create a full length chimeric BVDV-NADL/P-$E^{rns}$ genome by PCR with Oligo B-5 and Oligo 84.

For construction of chimeric BVDV-NADL/P-$E^{rns}$ DNA, a fragment of BVDV-NADL encoding for the 5'UTR to the 3' end of C gene was amplified by PCR from methylated plasmid with primers Oligo B-5 and Oligo 135. The P-$E^{rns}$ gene was amplified by PCR from the plasmid DNA containing P-$E^{rns}$ gene with Oligo 136 and Oligo 137, A BVDV fragment encoding for E1 to the 3'UTR was amplified by PCR from methylated plasmid with Oligo 138 and Oligo 84. The PCR products were gel purified with QIAquick Gel Extraction Kit. The purified PCR products were treated with Dpn I and Exonuclease 1. The treated PCR products were assembled to create a full length chimeric BVDV-NADL/P-$E^{rns}$ genome by PCR with Oligo B-5 and Oligo 84.

For sequence confirmation of the chimeric $E^{rns}$ regions, a fragment corresponding to the 5' UTR to the E1 region of each assembled full length chimeric genome was amplified by PCR using Oligo B-5 and Oligo 175, and the PCR products were sequenced and analyzed.

Full length viral genomic RNA transcripts were generated from plasmid containing the full-length cDNA of BVDV-NADL or chimeric BVDV-NADL/$E^{rns}$ DNAs using mMessage mMachine T7 Ultra kit (Ambion; Austin, Tex.). Quality and quantity of each RNA transcript was determined on an RNA gel and a Nanodrop spectrophotometer (Nanodrop; Wilmington, Del.). Overnight cultures of RD cells in wells of 6-well plates were transfected with viral RNA using Lipofectin reagent (Invitrogen) according to the manufacturer's instructions. Following transfection, the cells were incubated at 37° C. for 3 days. The supernatants were harvested and stored at −80° C.

Viral RNAs from harvested supernatants were extracted using MagMax™ AI/ND Viral RNA Isolation Kit (Ambion) according to the manufacturer's instructions. The RNAs were reverse transcribed and the region of each chimera encoding $N^{pro}$ to E1 was amplified using primers Oligo 177 and Oligo 175 (Table 1), and the ThermoScript™ RT-PCR System (Invitrogen) according to the manufacturer's instructions. The RT-PCR products were then sequenced.

Cell monolayers from either a viral RNA transfection or virus infection were fixed in 80% acetone. BVDV- or BDV-specific monoclonal antibodies (Mabs) were used in conjunction with the anti-mouse IgG peroxidase ABC Elite kit (Vector Laboratories; Burlingame, Calif.). Color was developed using VIP peroxidase substrate (Vector Laboratories).

Chimeric virus titers were determined by a limiting dilution method, Viral samples were 10-fold serially diluted and transferred to 96-well plates (100 μl per well), with 4-6 replicates per dilution. 100 μl of a suspension of BK-6 cells were then added to each well, and the plates incubated at 37° C. for 4-5 days. Virus infection was determined by both cytopathic effect (CPE) and MAb staining, Virus titers were calculated using the Spearman-Kärber method.

To obtain the biological clones of each chimera, virus samples were first diluted 100-fold and followed by a 10-fold dilution series. 100 μl of the diluted viruses were transferred to each well of a 96 well plate, 4 replicates per dilution. 100 μl of BK-6 cells were then added to each well, and the plates incubated at 37° C. for 4 days. The supernatants were harvested and transferred to new plates and stored at −80° C. The cells were fixed and stained. The supernatants from wells containing single virus foci were harvested and expanded as virus stocks.

Growth kinetics studies were carried out in T-25 flasks containing BK-6 cells. When the cells reached approximately 90% confluency, they were infected with each chimera at MOI of 0.02. After adsorption for 1 hr, the inoculum was removed. Cells were washed 3× with PBS, and 3 ml of fresh growth medium was then added. Samples were then collected at various time points from 0 to 144 hrs for titer determinations.

For the virus neutralization test, frozen stocks of the three BVDV-NADL/$E^{rns}$ chimeras, parental BVDV-NADL, and BVDV-CM5960 (BVDV type I) were diluted in DMEM to about 4,000 $TCID_{50}$/ml. Sera from cattle immunized with Bovi-Shield Gold (Pfizer; New York, N.Y.), with pre-determined titers against both BVDV type I and II, were 2-fold serially diluted with DMEM. 50 μl of virus (200 $TCID_{50}$) were mixed with an equal volume of diluted cattle serum in 96-well tissue culture plates (4 replicates/dilution), and incubated at 37° C. for 60 min. 100 μl of BK-6 cells were then added to each well, and the plates were incubated at 37° C. for 3-6 days. Serum negative for BVDV antibodies was also included in each plate as a control. End point neutralization titers of the sera were determined by both CPE and by immunohistochemistry (IHC) at day 3 and day 6.

Results.

Chimeric BVDV-NADL/$E^{rns}$ DNAs in which the NADL $E^{rns}$ gene/protein was replaced by $E^{rns}$ of giraffe (G-$E^{rns}$), reindeer (R-$E^{rns}$) or pronghorn antelope (P-$E^{rns}$) pestivirus, were constructed. Plasmid DNA containing each of the chimeric $E^{rns}$ regions was sequenced to confirm sequence authenticity. The following chimeric pestiviruses were deposited with the American Type Culture Collection (ATCC®), 10801 University Blvd., Manassas, Va., 20110, USA on Apr. 2, 2009, and confirmed viable by the ATCC® on Apr. 23, 2009: BVDV-NADL/G-$E^{rns}$ (PTA-9938), BVDV-NADL/P-$E^{rns}$ (PTA-9939), and BVDV-NADL/R-$E^{rns}$ (PTA-9940).

BVDV-NADL/$E^{rns}$ chimeric viruses were rescued from RD cells after transfection with in vitro-transcribed viral RNA. Extensive cytopathic effect (CPE) in RD cells was observed 48-72 hours after transfection with BVDV-NADL/G-$E^{rns}$ or BVDV-NADL/R-$E^{rns}$ RNA transcripts. CPE was not obvious with the BVDV-NADL/P-$E^{rns}$ virus, however. Culture supernatants were harvested from each well, and the remaining cells were fixed and stained with BVDV NS3-specific MAb antibody 20.10.6. Cells infected with one of the three chimeric pestiviruses were incubated with the MAb. Viral RNAs were extracted from the harvested supernatants, and sequenced to confirm the $E^{rns}$ genes of all three chimeras.

The three BVDV-NADL/$E^{rns}$ chimeras were tested for their reactivity to each of several $E^{rns}$ MAbs specific for BVDV or BDV. The results are shown in Table 2. The BVDV-NADL/R-$E^{rns}$ chimera reacted to all three BDV $E^{rns}$ Mabs, while neither BVDV-NADL/G-$E^{rns}$, BVDV-NADL/P-$E^{rns}$ nor BVDV-NADL parental virus were recognized by BDV $E^{rns}$ MAbs. BVDV-NADL/G-$E^{rns}$, BVDV-NADL/R-$E^{rns}$, and NADL parental virus reacted to a pan-BVDV $E^{rns}$ MAb 15C5. MAbs specific to either $E^{rns}$ of BDV or BVDV did not react with the BVDV-NADL/P-$E^{rns}$ chimera.

TABLE 2

Reactivity of BVDV-NADL/$E^{rns}$ chimeras to MAbs

| MAb | Specificity | Chimera reactivity: BVDV-NADL/G-$E^{rns}$ | BVDV-NADL/R-$E^{rns}$ | BVDV-NADL/P-$E^{rns}$ | BVDV-NADL |
|---|---|---|---|---|---|
| WS 371 | BDV $E^{rns}$ | − | +++ | − | − |
| WS 373 | BDV $E^{rns}$ | − | +++ | − | − |
| WS363 | BDV $E^{rns}$ | − | +++ | − | − |
| 15C5 | BVDV $E^{rns}$ | +++ | +++ | − | +++ |
| 20.10.6 | Pestivirus NS3 | +++ | +++ | ++ | +++ |

In order to determine whether the chimeric $E^{rns}$ proteins in the viruses had any impact on the recognition of viral neutralizing epitopes by antibodies from BVDV-vaccinated cattle, a virus neutralization assay was performed with the three BVDV-NADL/$E^{rns}$ chimeras, BVDV-NADL, and BVDV-CM5960 (BVDV type I). Sera from 4 cows with neutralizing antibody titers ranging from 0 to greater than 40,000 (determined previously against BVDV-CM5960) were utilized. The results (Table 3) indicate that titers against all three chimeras were generally comparable to those for parental BVDV-NADL and BVDV-CM5960. The neutralization titers against BVDV-NADL/P-$E^{rns}$ were slightly lower than those against the other two chimeras, BVDV-NADL and BVDV-CM5960.

TABLE 3

Neutralization titers of bovine antisera against BVDV-NADL/$E^{rns}$ chimeras

| Cattle Sera # | Neutralization titers: BVDV-NADL/G-$E^{rns}$ | BVDV-NADL/R-$E^{rns}$ | BVDV-NADL/P-$E^{rns}$ | BVDV-NADL | CM5960 |
|---|---|---|---|---|---|
| 816 | <10 | <10 | <10 | <10 | <10 |
| 77 | 320 | 320 | 320 | 160 | 320 |
| 1281 | 6400 | 12800 | 3200 | 3200 | 25600 |
| 1434 | 51200 | 25600 | 6400 | 25600 | 51200 |

The three BVDV-NADL/$E^{rns}$ chimeras were biologically cloned two times by limiting dilution. Three clones of BVDV-NADL/G-$E^{rns}$, four of BVDV-NADL/R-$E^{rns}$, and three of BVDV-NADL/P-$E^{rns}$ were obtained. These clones were each expanded between 1-3 times. Titration results indicated that expanded BVDV-NADL/G-$E^{rns}$ clone 1, BVDV-NADL/R-$E^{rns}$ clones 3 and 5, and BVDV-NADL/P-$E^{rns}$ clone 2 yielded the highest titers.

Growth kinetics studies were performed with BVDV-NADL/G-$E^{rns}$ clone 1, BVDV-NADL/R-$E^{rns}$ clone 3, BVDV-NADL/P-$E^{rns}$ clone 2, and uncloned BVDV-NADL/P-$E^{rns}$. Growth curves generated from these clones were compared to the parental BVDV-NADL. BVDV-NADL/G-$E^{rns}$ and BVDV-NADL/R-$E^{rns}$ chimeras had growth kinetics similar to the parental BVDV-NADL, while BVDV-NADL/P-$E^{rns}$ grew slower and had lower titers at each time point than the parental virus and other two chimeras.

Three BVDV-NADL/$E^{rns}$ chimeric viruses were created, in which the NADL $E^{rns}$ gene/protein was replaced by $E^{rns}$ of a giraffe, reindeer or pronghorn antelope pestivirus. All three chimeras were viable and infectious in both RD and BK-6 cells. In vitro data demonstrated that the chimeric $E^{rns}$ proteins did not affect neutralization of the chimeras by antisera from BVDV-vaccinated cattle. This suggests that neutralizing epitopes on the chimeric viruses, regardless of where they are located, were not affected by the $E^{rns}$ substitutions.

The chimeric viruses had different growth kinetics and reacted differently to BVDV or BDV $E^{rns}$ monoclonal antibodies. BVDV-NADL/G-$E^{rns}$ and BVDV-NADL/R-$E^{rns}$ had similar growth kinetics to the parental virus, while BVDV-NADL/P-$E^{rns}$ grew slower and to a lower titer than the parental virus. Both BVDV-NADL/G-$E^{rns}$ and BVDV-NADL/R-$E^{rns}$ reacted to BVDV $E^{rns}$ monoclonal antibody 15C5, while BVDV-NADL/P-$E^{rns}$ did not. Sequence comparison results showed that G-$E^{rns}$ and R-$E^{rns}$ had higher sequence similarities to BVDV NADL (75.8% and 76.2%, respectively) than P-$E^{rns}$ (59%). These data, taken together with the MAb reactivity results, suggest that G-$E^{rns}$ and R-$E^{rns}$ may be antigenically more similar to the parental $E^{rns}$ than P-$E^{rns}$.

EXAMPLE 2

Construction and Serological Characterization and Efficacy Testing of Chimeric Pestivirus Vaccine Candidates Type 1 BVDV strain CM5960 and Type 2 BVDV strain CM53637 were obtained from Pfizer Global Manufacturing. The viral RNAs were extracted using MagMax™ AI/ND Viral RNA Isolation Kit (Ambion) according to the manufacturer's instructions. The RNAs were reverse transcribed to generate cDNAs using ThermoScript™ RT-PCR System (Invitrogen) according to the manufacturer's instructions, Chimeric pestiviruses were generated by replacing the $E^{rns}$ gene of CM5960 and CM53637 with the $E^{rns}$ gene of pronghorn antelope pestivirus (P-$E^{rns}$) using an overlapping PCR method. The oligonucleotide primers used for PCRs are listed in Table 1.

For construction of chimeric CM5960/P-$E^{rns}$ DNA, a fragment of CM5960 cDNA between the 5'UTR and the 3' end of C gene was amplified by PCR from CM5960 cDNA with primers Oligo B-5 and Oligo 135. The P-$E^{rns}$ gene was amplified by PCR from the plasmid DNA containing P-$E^{rns}$ gene with Oligo 136 and Oligo 137. A third fragment between the beginning of E1 and the 3' end of E2 was amplified by PCR from CM5960 cDNA with primers Oligo 138 and Oligo 237.

The above-described fragments were gel purified using a QIAquick Gel Extraction Kit (Qiagen), and assembled by PCR to create one fragment with Oligo B-5 and Oligo 237. A fragment between E1 region and NS5B region was amplified by PCR from CM5960 cDNAs with primers Oligo P7 and Oligo P8. Another fragment between NS5A region and the end of 3'UTR was amplified by PCR from CM5960 cDNAs with primers Oligo P3 and Oligo 84. These three fragments were then gel purified, and assembled by PCR with Oligo B-5 and Oligo 84 to create a full length chimeric CM5960L/P-$E^{rns}$ genome.

For construction of chimeric CM53637/P-$E^{rns}$ DNA, a fragment of CM53637 cDNA between the 5'UTR and the 3' end of C gene was amplified by PCR from CM53637 cDNA with primers Oligo 296-1 and Oligo 297. A second fragment between the beginning of E1 and the 3' end of E2 was amplified by PCR from CM53637 cDNA with primers Oligo 298 and Oligo 303. These two fragments were gel purified, and together with a fragment encoding for the P-$E^{rns}$ gene (see above), were assembled by PCR to create one fragment using Oligo 296-1 and Oligo 303.

A fragment between E1 region and NS3 region was then amplified by PCR from CM53637 cDNA with primers Oligo 298 and Oligo 299. Another fragment between NS3 region and the end of 3'UTR was also amplified by PCR from CM53637 cDNA with primers Oligo 300 and Oligo 92-1. These two fragments and the one above were gel purified, and assembled by PCR with Oligo 296-1 and Oligo 92-1 to create a full length chimeric CM53637/P-$E^{rns}$ genome.

Full length viral genomic RNA transcripts were generated from chimeric CM5960/P-$E^{rns}$ and chimeric CM53637/P-$E^{rns}$ DNAs using mMessage mMachine T7 Ultra kit (Ambion). Quality and quantity of each RNA transcript was determined on an RNA gel. Overnight cultures of RD cells in wells of 6-well plates were transfected with viral RNA using Lipofectin reagent (Invitrogen) according to the manufacturer's instructions. Following transfection, the cells were incubated at 37° C. for 3 days. The cells plus the supernatants were passed one to several times in RD and/or BK-6 cells. The supernatants were then serially passed in BK-6 cells. The supernatants were harvested and stored at −80° C.

To confirm the identity of rescued recombinant virus, viral RNAs from harvested supernatants were extracted using MagMax™ AI/ND Viral RNA Isolation Kit (Ambion) according to the manufacturer's instructions. The RNAs were reverse transcribed using ThermoScript™ RT-PCR System (Invitrogen) according to the manufacturer's instructions and the region of each chimera between 5' UTR and E2 or p7 was amplified by PCR using primers Oligo B-5 and Oligo 237 (for CM5960/P-$E^{rns}$ chimera) or Oligo 296-1 and Oligo 321 (for CM53637/P-$E^{rns}$ chimera) (Table 1), The RT-PCR products were then sequenced.

Cell monolayers from either a viral RNA transfection or virus infection were fixed in 80% acetone. BVDV specific MAbs were used in conjunction with the anti-mouse IgG peroxidase ABC Elite kit (Vector Laboratories) for immunohistochemistry. Color was developed using VIP peroxidase substrate (Vector Laboratories).

Results.

Chimeric CM5960/P-$E^{rns}$ and CM53637/P-$E^{rns}$ viruses were constructed and rescued. The 5'UTR to E2 regions, including the chimeric pronghorn-$E^{rns}$ regions, were confirmed by sequencing. Both chimeras were viable and infectious in both RD and BK-6 cells. Both chimeras were not reactive to BVDV $E^{rns}$ specific MAb 15C5, but reactive to BVDV NS3 specific MAb 20.10.6 in immunohistochemistry staining.

The sequence for the chimeric pestivirus (BVDV-CM5960 (BVDV type 1)/P-$E^{rns}$) is presented in the sequence listing as SEQ ID NO: 31. The sequence for the chimeric pestivirus (BVDV-CM53637 (BVDV type II/P-$E^{rns}$) is presented in the sequence listing as SEQ ID NO: 32.

The CM5960/P-$E^{rns}$ chimera was biologically cloned by limited dilution (see above Example 1 for methodology).

EXAMPLE 3

Efficacy Testing of Chimeric Pestivirus Vaccine Candidates in a Calf Respiratory Disease Model BVDV negative healthy calves are obtained, randomly assigned to study groups, and maintained under supervision of an attending veterinarian. The test vaccine is combined with a sterile adjuvant, and administered by either intramuscular (IM) or subcutaneous (SC) injection, or by intranasal (IN) inoculation. The vaccine is given either as one or two doses. Two doses of vaccine are administered, 21 to 28 days apart. The animals are subsequently challenged at 21 to 28 days following the final vaccination with a Type 1 or Type 2 strain of BVDV. Challenge inoculum is given intranasally in a 4 ml divided dose, 2 ml per nostril. Control groups consisting of unvaccinated, unchallenged animals and/or unvaccinated, challenged animals are also maintained throughout the study.

Clinical parameters are monitored daily, including rectal temperature, depression, anorexia, and diarrhea. Serum neutralization titers are determined by a constant-virus, decreasing-serum assay in bovine cell culture, using serial dilutions of serum combined with a BVDV Type 1 or 2 strain. Post-challenge isolation of BVDV in bovine cell culture is attempted from peripheral blood. A BVDV-positive cell culture is determined by indirect immunofluorescence. To demonstrate protection following challenge, a reduction in incidence of infection is demonstrated in vaccinated groups versus the control groups.

EXAMPLE 4

Chimeric Pestivirus Vaccine Efficacy Testing in a Pregnant Cow-Calf Model

BVDV-negative cows and heifers of breeding age are obtained and randomly assigned to a vaccination test group or a placebo (control) group. Cows are inoculated twice by intramuscular (IM) or subcutaneous (SC) injection, with either vaccine or placebo, 21 to 28 days apart. Following the second vaccination, all cows receive an IM prostaglandin injection to synchronize estrus. Cows displaying estrus are bred by artificial insemination with certified BVDV-negative semen. At approximately 60 days of gestation, the pregnancy status of cows is determined by rectal palpation.

Approximately 6 weeks later, cows with confirmed pregnancies are randomly selected from each test group. Each of these cows is challenged by intranasal inoculation of BVDV Type 1 or 2. Blood samples are collected on the day of challenge and at multiple postchallenge intervals for purposes of BVDV isolation.

Twenty-eight days after challenge, left flank laparotomies are performed and amniotic fluid is extracted from each cow. Immediately prior to surgery, a blood sample is collected from each cow for serum neutralization assays. Following caesarian delivery, a blood sample is collected from each fetus. Fetuses are then euthanized, and tissues are aseptically collected for purposes of BVDV isolation. In cases where spontaneous abortions occur, blood samples are taken from the dam when abortion is detected and two weeks later. The paired blood samples and aborted fetuses are subjected to serologic testing and virus isolation. Vaccine efficacy is demonstrated by a lack or decrease of fetal infection and late-term abortion.

EXAMPLE 5

Diagnostic Assays for Differentiation Between Vaccinated and Naturally Infected Cattle Cattle vaccinated with a vaccine of the present invention can be compared with cattle naturally infected with a wild type BVDV. Cattle of various ages are vaccinated with either a live or inactivated chimeric pestivirus vaccine according to instructions provided. Serum samples are collected 2-3 weeks or later following vaccination. To differentiate between cattle which received the chimeric pestivirus vaccine versus those infected by a field (wild-type) strain of BVDV, serum samples are tested via a differential diagnostic assay. The chimeric pestivirus elicits the production of specific antibodies which bind to the $E^{rns}$ protein of the chimeric pestivirus, but not to the $E^{rns}$ protein present on wild-type BVDV. In the context of wild-type BVDV, the opposite is true. Specific antibodies are generated which recognize the $E^{rns}$ protein present on wild-type BVDV, but not the $E^{rns}$ protein present on the chimeric pestivirus. Methods of assaying for antibody binding specificity and affinity are well known in the art, and include but are not limited to immunoassay formats such as competitive ELISA, direct peptide ELISA, Western blots, indirect immunofluorescent assays, and the like.

For a competitive ELISA, whole or partial wild-type or chimeric pestivirus viral antigens, including the $E^{rns}$ protein (naturally, synthetically or recombinantly derived), are used as an antigen source. Following coating of the ELISA plate with antigen under alkaline conditions, cattle serum samples and dilutions are added together with an optimized dilution of a MAb specific for either $E^{rns}$ protein of the wild type BVDV or the $E^{rns}$ protein of the chimeric pestivirus, and incubated for 30-90 min. Either horseradish peroxidase or alkaline phosphatase is conjugated to the MAb to allow for colorimetric detection of binding. Following washing of the plates, an enzyme-specific chromogenic substrate is added, and after a final incubation step, the optical density of each well is measured at a wavelength appropriate for the substrate used. The degree of inhibition of binding of the labeled mAb is dependent on the level of antibodies in the cattle serum that specifically recognize the protein coating the plate.

In the case of chimeric $E^{rns}$ protein (e.g. pronghorn $E^{rns}$) present on the chimeric pestivirus being the test antigen, a lack of binding by the chimeric pestivirus $E^{rns}$-specific mAb indicates the presence of antibodies in the cattle serum that recognize the chimeric pestivirus-specific epitope, indicative of vaccination. In contrast, serum from cattle not immunized, but naturally infected, will not contain antibodies which will bind to the chimeric pestivirus $E^{rns}$ protein coating the plate. Therefore, the chimeric pestivirus $E^{rns}$-specific mAb will bind to the bound protein, and result in subsequent color development.

In the case of $E^{rns}$ protein present on wild-type BVDV being the test antigen, a lack of binding by the wild type BVDV $E^{rns}$-specific mAb indicates the presence of antibodies in the cattle serum that recognize the wild-type BVDV-specific epitope, indicative of a natural (wild-type) infection. In contrast, serum from cattle immunized with the chimeric pestivirus vaccine will not contain antibodies which will bind to the wild-type BVDV $E^{rns}$ protein coating the plate. Therefore, the wild type BVDV $E^{rns}$-specific mAb will bind to the bound protein, and result in subsequent color development. For development of such an assay, the following methods were carried out.

First, a recombinant baculovirus expressing BVDV-NADL $E^{rns}$ was constructed. A portion of the C protein of BVDV, plus the full length $E^{rns}$ gene, were amplified by PCR from a plasmid containing full length of BVDV-NADL cDNA with primers Oligo 250 (SEQ ID NO: 29; 5'-CACCATGAAAATAGTGCCCAAAGAATC-3') and Oligo 252 (SEQ ID NO: 30; 5'-TTAAGCGTATGCTCCAAACCACGTC-3'). The PCR product was cloned into pENTR™/D-TOPO (Invitrogen) and transformed into One Shot® Competent *E. coli* (Invitrogen) according to the manufacturer's instructions. The recombinant plasmid was extracted and the insert was confirmed by sequencing. This plasmid was designated pENTR-$E^{rns}$. pENTR-$E^{rns}$ and BaculoDirect™ Baculovirus Expression System (Invitrogen) were used to construct recombinant baculovirus expressing BVDV-NADL $E^{rns}$ according to the manufacturer's instructions. The recombinant baculovirus expressing BVDV-NADL $E^{rns}$ was generated, plaque purified, expanded, and stored at both 4° C. and −80° C. The expression of BVDV-NADL $E^{rns}$ in the recombinant baculovirus was confirmed by immunofluorescent staining and Western blotting against BVDV $E^{rns}$ specific MAb 15C5 following conventional Western Blot methods.

For production of the ELISA antigen, SF21 cells in 100 ml suspension culture were infected with 0.5 ml of the recombinant baculovirus stock. The cells were harvested after 4 days incubation at 27° C. The cells were centrifuged at low speed (about 800 g) for 10 min to collect the cells and washed once with PBS. The cells were lysed with 150 mM NaCl, 50 mM Tris HCl pH 8.0, and 1% IGEPAL CA-630. The mixture was first incubated on ice for 10 minutes and then at −80° C. for 1 hour. After thawing, the mixture was clarified by centrifugation at 1000 g for 15 minutes. The supernatant was further clarified by centrifuge at 8000 g for 20 minutes at 4° C. The final supernatant, designated Baculo-$E^{rns}$ lysate, was aliquoted and stored at −80° C.

In carrying out the assay, the ELISA plates were coated overnight at 4° C. with 100 μl/well of MAb WB210 (Veterinary Laboratory Agency; Type 1 BVDV $E^{rns}$ specific), diluted 1:1000 in carbonate/bicarbonate buffer (pH 9.0). The next day, the plates were washed three times and blocked with blocking buffer (PBS containing 1% casein sodium salt and 0.05% Tween 20) at 37° C. for 1 hour. The plates were subsequently washed three times with blocking buffer, and 100 μl of Baculo-$E^{rns}$ lysate (1:3200 diluted in PBS) was added to each well, and the plates were incubated at 37° C. for 1 hour. Following three washes with blocking buffer, 100 μl of undiluted cattle serum samples were added to the wells, except for one column of wells (to serve as non-competing 15C5-HRP controls), and incubated at 37° C. for 1 hour. Following three more washes with blocking buffer, 100 μl of MAb 15C5-HRP conjugate (BVDV $E^{rns}$ specific, 1:20,000 diluted in blocking buffer) was added to each well, and incubated at 37° C. for 1 hour. Following three washes with blocking buffer, 100 μl of ABTS substrate (Peroxidase substrate solutions A+B; KPL, USA) was added to each well, and incubated at room temperature for 20-60 minutes for color development. The optical density (OD) was measured at the wavelength of 405 nm. The percentage of OD reduction for each serum sample is calculated by following formula:

$$[1-(\text{OD of Sample} \div \text{Mean OD of 15C5-HRP Controls})] \times 100\%.$$

Results:

All of the serum samples that tested positive by the virus neutralization (VN) test had over 82% O.D. reduction, except sample ID#13851 (Table 4). All of the serum samples that tested negative by the virus neutralization test had less than 17% O.D. reduction, except sample ID#5150 (Table 4). The discrepancy might be explained by the differences in how the assays are carried out, as they are measuring different antibodies, and the proportion of specific antibodies varies among animals.

TABLE 4

BVDV positive and negative serum samples in a MAb15C5 competition ELISA.

| Row # | Sample ID | O.D. of Sample | Average O.D. of No Serum Column | % Reduction |
|---|---|---|---|---|
| 1 | 40021 | 0.0615 | 0.907013 | 93.21950182 |
| 2 | 40014 | 0.0965 | 0.907013 | 89.36068171 |
| 3 | 40422 | 0.0639 | 0.907013 | 92.95489701 |
| 4 | 40372 | 0.0754 | 0.907013 | 91.68699897 |
| 5 | 40222 | 0.0634 | 0.907013 | 93.01002301 |
| 6 | 40152 | 0.0894 | 0.907013 | 90.14347093 |
| 7 | 13461 | 0.0663 | 0.907013 | 92.6902922 |
| 8 | 13851 | 0.641 | 0.907013 | 29.32846607 |
| 9 | 13801 | 0.1599 | 0.907013 | 82.37070472 |
| 10 | 13904 | 0.073 | 0.907013 | 91.95160378 |
| 11 | 40504 | 0.0625 | 0.907013 | 93.10924981 |
| 12 | 40471 | 0.0914 | 0.907013 | 89.92296693 |
| 13 | 35037 | 0.0639 | 0.907013 | 92.95489701 |
| 14 | 13690 | 0.159 | 0.907013 | 82.46993152 |
| 15 | 13797 | 0.0859 | 0.907013 | 90.52935294 |
| 16 | 6127 | 0.0886 | 0.907013 | 90.23167253 |
| 17 | 5138 | 0.7434 | 0.907013 | 18.03866097 |
| 18 | 5139 | 0.8423 | 0.907013 | 7.13473787 |
| 19 | 5141 | 0.7732 | 0.907013 | 14.75315128 |
| 20 | 5142 | 0.7475 | 0.907013 | 17.58662776 |
| 21 | 5144 | 0.8293 | 0.907013 | 8.568013909 |
| 22 | 5145 | 0.9488 | 0.907013 | −4.607100449 |
| 23 | 5146 | 0.9451 | 0.907013 | −4.199168038 |
| 24 | 5147 | 1.0138 | 0.907013 | −11.77348064 |
| 25 | 5148 | 0.9322 | 0.907013 | −2.7769172 |
| 26 | 5149 | 0.9794 | 0.907013 | −7.980811741 |
| 27 | 5150 | 0.1157 | 0.907013 | 87.24384325 |

Rows 1-16: Positive cattle serum samples
Rows 17-27: Negative cattle serum samples
All serum samples are used undiluted in the ELISA Although the present invention has been described in considerable detail with reference to certain versions thereof, other versions are possible. Therefore, the scope of the appended claims should not be limited to the description of the versions contained herein.

We claim:

1. A chimeric bovine viral diarrhea virus (BVDV), that comprises pronghorn antelope pestivirus $E^{rns}$ protein, and lacks BVDV $E^{rns}$ protein.

2. A culture of the bovine viral diarrhea virus of claim 1.

3. An isolated host cell comprising the bovine viral diarrhea virus of claim 1.

4. A polynucleotide molecule encoding for the bovine viral diarrhea virus of claim 1.

5. An immunogenic composition comprising the bovine viral diarrhea virus of claim 1 and a veterinarily-acceptable carrier.

6. The immunogenic composition of claim 5, wherein the veterinarily-acceptable carrier is an adjuvant.

7. The immunogenic composition of claim 5, wherein said bovine viral diarrhea virus is live attenuated.

8. The immunogenic composition of claim 5, wherein said bovine viral diarrhea virus is inactivated.

9. The immunogenic composition of claim 5, further comprising one or more additional antigens useful for treating or preventing the spread of one or more additional pathogenic microorganisms in a bovine.

10. An immunogenic composition comprising the polynucleotide molecule of claim 4 and a veterinarily-acceptable carrier.

11. A vaccine comprising the bovine viral diarrhea virus of claim 1 and a veterinarily-acceptable carrier.

12. The vaccine of claim 11, wherein the veterinarily-acceptable carrier is an adjuvant.

13. The vaccine of claim 11, wherein said bovine viral diarrhea virus is live attenuated.

14. The vaccine of claim 11, wherein said bovine viral diarrhea virus is inactivated.

15. A vaccine comprising the polynucleotide molecule of claim 4 and a veterinary acceptable carrier.

16. The vaccine of claim 11, further comprising one or more additional antigens useful for treating or preventing the spread of one or more additional pathogenic microorganisms in a bovine.

17. A kit comprising, in at least one container, the vaccine of claim 11.

18. A method of vaccinating an animal, wherein a DIVA pestivirus vaccine is administered to said animal, and wherein said DIVA pestivirus vaccine comprises the chimeric pestivirus of claim 1, further wherein said chimeric pestivirus has at least one $E^{rns}$ epitope which is not present in wild-type bovine viral diarrhea virus.

19. A method of vaccinating an animal, wherein a DIVA pestivirus vaccine is administered to said animal, and wherein said DIVA vaccine comprises the chimeric pestivirus of claim 1, further wherein said chimeric pestivirus lacks at least one $E^{rns}$ epitope which is present in wild-type bovine viral diarrhea virus.

20. A diagnostic kit for differentiating between an animal vaccinated with a vaccine comprising the bovine viral diarrhea virus of claim 1 and an animal infected with wild type bovine viral diarrhea virus, said kit comprising reagents capable of detecting pronghorn antelope $E^{rns}$ protein which is present in the chimeric pestivirus of the vaccine, but which is not present in wild-type bovine viral diarrhea virus.

21. The chimeric virus of claim 1, wherein the BVDV is type I.

22. The chimeric virus of claim 1, wherein the BVDV is type II.

23. The vaccine of claim 11, comprising chimeric type I bovine viral diarrhea virus SEQ ID NO: 31.

24. The vaccine of claim 11, comprising chimeric type II bovine viral diarrhea virus SEQ ID NO: 32.

* * * * *